(12) United States Patent
Liang et al.

(10) Patent No.: US 7,662,606 B1
(45) Date of Patent: Feb. 16, 2010

(54) β-AGARASE ISOLATED FROM *THALASSOMONAS AGARIVORANS*, PREPARATION PROCESS AND USES THEREOF

(75) Inventors: Shu-Shan Liang, Hsinchu (TW); Yi-Hong Chen, Hsinchu (TW); Li-Ling Liaw, Hsinchu (TW)

(73) Assignee: Food Industry Research & Development Institute, Hsinchu (TW)

( * ) Notice: Subject to any disclaimer, the term of this patent is extended or adjusted under 35 U.S.C. 154(b) by 32 days.

(21) Appl. No.: 12/243,714

(22) Filed: Oct. 1, 2008

(51) Int. Cl.
*C12N 9/26* (2006.01)
*C12N 9/42* (2006.01)
*C12P 19/04* (2006.01)
*C07H 21/04* (2006.01)

(52) U.S. Cl. ............... 435/201; 435/209; 435/101; 435/810; 435/975; 536/23.2

(58) Field of Classification Search ............... None
See application file for complete search history.

(56) References Cited

U.S. PATENT DOCUMENTS

2004/0132036 A1* 7/2004 Tomono et al. ............... 435/6

OTHER PUBLICATIONS

Ekborg et al., Genomic and Proteomic analyses of the Agarolytic system expressed by *Saccharophagus degradans* 2-40. 2006, vol. 72 (5): 3396-3405.*
Ohta et al., High-level expression of a neoagarobiose-producing beta-agarase gene from Agaivorans sp. JAMB-A11 in *Bacillus subtilis* ... Biotechnol. Appl. Biochem., 2005, vol. 41: 183-191.*
Kisselev L., Polypeptide release factors in prokaryotes and eukaryotes: same function, different structure. Structure, 2002, vol. 10: 8-9.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of a b-ketoacyl synthase to a malonyl decarboxylase by replacement of the active-site cysteine with glutamine. Biochemistry, 1999, vol. 38: 11643-11650.*
Seffernick et al., Melamine deaminase and Atrazine chlorohydrolase: 98 percent identical but functionally different. J. Bacteriol.,2001, vol. 183 (8): 2405-2410.*
Guo et al., Protein tolerance to random amino acid change. PNAS., 2004, vol. 101 (25): 9205-9210.*
Schroeder, D. C., Jaffer, M. A., Coyne, V. E. (2003) Investigation of the role of A β(1-4) agarase produced by *Pseudoalteromonas gracilis* B9 in eliciting disease symptoms in the red alga *Gracilaria gracilis*. *Microbiology* 149: 2919-2929.
Allouch, J., Jam, M., Helbert, W., Barbeyron, T., Kloareg, B., Henrissat, B. And Czjzek, M. (2003) The three-dimensional structures of two β-agarases. *J. Biol. Chem.* 278: 47171-47180.
Sugano, Y., Matsumoto, T., Kodama, H. and Noma, M. (1993a) Cloning and sequencing of *aga A*, a unique agarase 0107 gene from a marine bacterium, *Vibrio* sp. strain JT0107. *Appl. Environ. Microbiol.* 59: 3750-3756.
Belas, R., Bartlett, D. and Michael, S. (1988) Cloning and gene replacement mutagenesis of a *Pseudomonas atlantica* agarase gene. *Appl. Environ. Microbiol.* 54: 30-37.
Ohta, Y., Hatada, Y., Nogi, Y., Li, Z., Ito, S. and Horikoshi, K. (2004) Cloning, expression, and characterization of a glycoside hydrolase family 86 β-agarase from a deep-sea Microbulbifer-like isolate. *Appl. Microbiol. Biotechnol.* 66: 266-275.
Yoshizawa, Y., Ametani, A., Tsunehiro, J., Nomura, K., Itoh, M., Fukui, F. and Kaminogawa, S. (1995) Macrophage stimulation activity of thepolysaccharide fraction from a marine alga (*Porphyra yezoensis*):structure-function relationships and improved solubility. *Biosci. Biotechnol. Biochem.* 59: 1933-1937.
Kobayashi, R., Takisada, M., Suzuki, T., Kirimura, K. and Usami, S. (1997) Neoagarobiose as a novel moisturizer with whitening effect. *Biosci. Biotechnol. Biochem.* 61: 162-163.
Araki, T., Lu, Z. and Morishita, T. (1998) Optimization of parameters for isolation of protoplasts from *Gracilaria verrucosa* (Rhodophyta). *J. Mar. Biotechnol.* 6: 193-197.
Jean, W. D., Shieh, W. Y. And Liu, T.Y. (2006) *Thalassomonas agarivorans* sp. nov., a marine agarolytic bacterium isolated from shallow coastal water of An-Ping Harbour, Taiwan, and emended description of the genus *Thalassomonas*. *Int. J. Syst. Evol. Microbiol.* 56: 1245-1250.
Hatada, Y., Ohta, Y. and Horikoshi K. (2006) Hyperproduction and application of β-agarase to enzymatic hancement of antioxidant activity of porphyran. *J. Agric. Food Chem.* 54: 9895-9900.

* cited by examiner

*Primary Examiner*—Ganapathirama Raghu
(74) *Attorney, Agent, or Firm*—Sughrue Mion, PLLC

(57) ABSTRACT

The present invention relates to the cloning and expression of a novel β-agarase gene, agaB1, and a novel β-agarase, AgaB1, encoded from the gene. The present invention also provides a method for producing the β-agarase, and the utilization of the β-agarase.

9 Claims, 15 Drawing Sheets

SEQUENCE LISTING

```
<160> NUMBER OF SEQ ID NOS: 6

<210> SEQ ID NO 1
<211> LENGTH: 2325
<212> TYPE: DNA
<213> ORGANISM: Thalassomonas agarivorans
<220> FEATURE:
<221> NAME/KEY: CDS
```

<222> LOCATION: (1)..(2325)

<400> SEQUENCE: 1

| | | | | | | | | | | | | | | | | |
|---|---|---|---|---|---|---|---|---|---|---|---|---|---|---|---|---|
| atg | cat | aat | aaa | atg | agt | aaa | cta | tgg | ttc | gct | agc | gct | atc | tca | tgc | 48 |
| Met | His | Asn | Lys | Met | Ser | Lys | Leu | Trp | Phe | Ala | Ser | Ala | Ile | Ser | Cys | |
| 1 | | | | 5 | | | | | 10 | | | | | 15 | | |
| cta | gca | ata | tta | gga | tgc | agc | caa | caa | gcg | tct | aat | gat | aat | aac | ggt | 96 |
| Leu | Ala | Ile | Leu | Gly | Cys | Ser | Gln | Gln | Ala | Ser | Asn | Asp | Asn | Asn | Gly | |
| | | | 20 | | | | | 25 | | | | | 30 | | | |
| gta | atc | gac | gaa | ctc | gtt | aat | ttt | tct | tca | caa | aca | aca | ctc | gat | caa | 144 |
| Val | Ile | Asp | Glu | Leu | Val | Asn | Phe | Ser | Ser | Gln | Thr | Thr | Leu | Asp | Gln | |
| | | | 35 | | | | | 40 | | | | | 45 | | | |
| aat | atc | gcc | tta | tat | aat | gcg | tct | acc | gaa | tat | aat | gca | gaa | aca | aga | 192 |
| Asn | Ile | Ala | Leu | Tyr | Asn | Ala | Ser | Thr | Glu | Tyr | Asn | Ala | Glu | Thr | Arg | |
| | 50 | | | | | 55 | | | | | 60 | | | | | |
| tca | cta | aaa | gta | aac | ttt | aat | aca | agt | gag | cac | gcg | tac | agt | tct | atc | 240 |
| Ser | Leu | Lys | Val | Asn | Phe | Asn | Thr | Ser | Glu | His | Ala | Tyr | Ser | Ser | Ile | |
| 65 | | | | | 70 | | | | | 75 | | | | | 80 | |
| tcg | ttt | gtc | tca | gaa | gcg | ggg | tgg | gat | tgg | agc | gat | tta | aac | gac | ttt | 288 |
| Ser | Phe | Val | Ser | Glu | Ala | Gly | Trp | Asp | Trp | Ser | Asp | Leu | Asn | Asp | Phe | |
| | | | | 85 | | | | | 90 | | | | | 95 | | |
| aat | ata | gcg | ttt | gat | att | gct | aac | gaa | ggt | gaa | cat | tca | acg | caa | gta | 336 |
| Asn | Ile | Ala | Phe | Asp | Ile | Ala | Asn | Glu | Gly | Glu | His | Ser | Thr | Gln | Val | |
| | | | 100 | | | | | 105 | | | | | 110 | | | |
| tac | tta | gat | ata | act | gat | ggc | aat | ggt | gac | aac | tat | acg | cga | agt | gta | 384 |
| Tyr | Leu | Asp | Ile | Thr | Asp | Gly | Asn | Gly | Asp | Asn | Tyr | Thr | Arg | Ser | Val | |
| | | | | 115 | | | | | 120 | | | | | 125 | | |
| agc | att | cct | gtt | ggc | gcc | acc | aaa | acc | tat | tac | gcc | aaa | atg | gcc | ggt | 432 |
| Ser | Ile | Pro | Val | Gly | Ala | Thr | Lys | Thr | Tyr | Tyr | Ala | Lys | Met | Ala | Gly | |
| | | 130 | | | | | 135 | | | | | 140 | | | | |
| cat | gac | ctg | caa | aca | cca | gac | ggt | gac | gaa | gac | gtt | gaa | tta | aat | ttt | 480 |
| His | Asp | Leu | Gln | Thr | Pro | Asp | Gly | Asp | Glu | Asp | Val | Glu | Leu | Asn | Phe | |
| 145 | | | | | 150 | | | | | 155 | | | | | 160 | |
| atg | tcc | ggt | ttg | cgt | tca | aat | cct | gat | aca | tgg | caa | tca | gat | gaa | gtt | 528 |
| Met | Ser | Gly | Leu | Arg | Ser | Asn | Pro | Asp | Thr | Trp | Gln | Ser | Asp | Glu | Val | |
| | | | | 165 | | | | | 170 | | | | | 175 | | |
| aac | ttt | att | tca | ttg | tgg | ggt | aag | aag | aac | cta | gat | gta | tca | aat | att | 576 |
| Asn | Phe | Ile | Ser | Leu | Trp | Gly | Lys | Lys | Asn | Leu | Asp | Val | Ser | Asn | Ile | |
| | | | 180 | | | | | 185 | | | | | 190 | | | |
| aaa | agg | att | gcc | ttt | agc | gtg | cag | agt | gcg | ctt | tac | gac | aaa | gct | atc | 624 |
| Lys | Arg | Ile | Ala | Phe | Ser | Val | Gln | Ser | Ala | Leu | Tyr | Asp | Lys | Ala | Ile | |
| | | 195 | | | | | 200 | | | | | 205 | | | | |
| acc | ttt | agt | aaa | gtg | cag | att | cga | caa | aat | cca | gcc | atg | gac | gaa | aca | 672 |
| Thr | Phe | Ser | Lys | Val | Gln | Ile | Arg | Gln | Asn | Pro | Ala | Met | Asp | Glu | Thr | |
| 210 | | | | | 215 | | | | | 220 | | | | | | |
| ttc | ctt | acc | ggc | atc | gtc | gac | caa | tat | gga | caa | aat | gct | aaa | caa | gaa | 720 |
| Phe | Leu | Thr | Gly | Ile | Val | Asp | Gln | Tyr | Gly | Gln | Asn | Ala | Lys | Gln | Glu | |
| 225 | | | | | 230 | | | | | 235 | | | | | 240 | |
| ttt | gtc | ggt | aaa | atc | cat | aat | gac | cag | gaa | ttg | cta | gcg | gct | cgt | gat | 768 |
| Phe | Val | Gly | Lys | Ile | His | Asn | Asp | Gln | Glu | Leu | Leu | Ala | Ala | Arg | Asp | |
| | | | | 245 | | | | | 250 | | | | | 255 | | |
| gaa | gag | cta | tca | gct | ttg | aaa | aat | ggt | tat | gac | gcc | gag | aca | aga | act | 816 |
| Glu | Glu | Leu | Ser | Ala | Leu | Lys | Asn | Gly | Tyr | Asp | Ala | Glu | Thr | Arg | Thr | |
| | | | 260 | | | | | 265 | | | | | 270 | | | |
| aag | ttt | ggc | ggt | tgg | aaa | aac | gga | cca | agg | caa | gaa | gct | aca | ggc | tat | 864 |
| Lys | Phe | Gly | Gly | Trp | Lys | Asn | Gly | Pro | Arg | Gln | Glu | Ala | Thr | Gly | Tyr | |
| | | 275 | | | | | 280 | | | | | 285 | | | | |
| ttt | aga | aca | gaa | aaa | atc | aat | gga | aag | tgg | tct | ttg | gtt | gat | cca | cta | 912 |
| Phe | Arg | Thr | Glu | Lys | Ile | Asn | Gly | Lys | Trp | Ser | Leu | Val | Asp | Pro | Leu | |
| | 290 | | | | | 295 | | | | | 300 | | | | | |

```
gga tat cct tat ttt gcc act ggg cta gat att atc cgc ctt tct aat        960
Gly Tyr Pro Tyr Phe Ala Thr Gly Leu Asp Ile Ile Arg Leu Ser Asn
305                 310                 315                 320 acg tcg acc atg aca ggg tac gat ttt gat cag ggt cta atc aac cag       1008
Thr Ser Thr Met Thr Gly Tyr Asp Phe Asp Gln Gly Leu Ile Asn Gln
                325                 330                 335 cgt aag gcg agt gac tta aca ccg gaa gat tct caa aag ctt aat cgt       1056
Arg Lys Ala Ser Asp Leu Thr Pro Glu Asp Ser Gln Lys Leu Asn Arg
            340                 345                 350 gtg agc aac gaa gca gcg aag aca aga tat gta gca tca gat ctt cgt       1104
Val Ser Asn Glu Ala Ala Lys Thr Arg Tyr Val Ala Ser Asp Leu Arg
        355                 360                 365 aag gac ctt ttt aca tgg tta cca agc tat gac gaa cca ttg ggt aag       1152
Lys Asp Leu Phe Thr Trp Leu Pro Ser Tyr Asp Glu Pro Leu Gly Lys
    370                 375                 380 cat tat ggt tat cgt cgc agt gca cac tct ggt cca ctt agc cac ggt       1200
His Tyr Gly Tyr Arg Arg Ser Ala His Ser Gly Pro Leu Ser His Gly
385                 390                 395                 400 gaa aca ttt agc ttt tac tct gcc aat cta gaa aga aaa tat gct gat       1248
Glu Thr Phe Ser Phe Tyr Ser Ala Asn Leu Glu Arg Lys Tyr Ala Asp
                405                 410                 415 atc aat cca gac ttt atg gaa gta tgg aag gac gtc acg att cgc aga       1296
Ile Asn Pro Asp Phe Met Glu Val Trp Lys Asp Val Thr Ile Arg Arg
            420                 425                 430 atg caa acc tgg gga ttt act tca ttc ggt aat tgg aca gat cct atg       1344
Met Gln Thr Trp Gly Phe Thr Ser Phe Gly Asn Trp Thr Asp Pro Met
        435                 440                 445 ttc tat caa aac gac cga gtc cca tat ttt gca aat ggc tgg att att       1392
Phe Tyr Gln Asn Asp Arg Val Pro Tyr Phe Ala Asn Gly Trp Ile Ile
    450                 455                 460 ggt aac tac aaa aaa gta tca agt ggc aat gat ttt tgg gcg cct ctg       1440
Gly Asn Tyr Lys Lys Val Ser Ser Gly Asn Asp Phe Trp Ala Pro Leu
465                 470                 475                 480 cca gat gtc ttt gac ccc ttg ttt gaa gag cgc gcc att gtg acc gta       1488
Pro Asp Val Phe Asp Pro Leu Phe Glu Glu Arg Ala Ile Val Thr Val
                485                 490                 495 aaa caa gtt gcg gct gaa gta caa aac aac cct tgg tgt gtt ggt gtt       1536
Lys Gln Val Ala Ala Glu Val Gln Asn Asn Pro Trp Cys Val Gly Val
            500                 505                 510 ttt att gac aac gaa atg agt ttt ggt cgt cca gac agt gtt gct tca       1584
Phe Ile Asp Asn Glu Met Ser Phe Gly Arg Pro Asp Ser Val Ala Ser
        515                 520                 525 cac tac ggt att gta cta aac aca ctt gca cgc gac ggt aaa gat gta       1632
His Tyr Gly Ile Val Leu Asn Thr Leu Ala Arg Asp Gly Lys Asp Val
    530                 535                 540 cca acc aaa gca gaa ttt acg cgc gta atg aaa gaa aag tat caa gat       1680
Pro Thr Lys Ala Glu Phe Thr Arg Val Met Lys Glu Lys Tyr Gln Asp
545                 550                 555                 560 atc gcc gcg cta aat aag gca tgg ggt acc gac atc gca agt tgg gac       1728
Ile Ala Ala Leu Asn Lys Ala Trp Gly Thr Asp Ile Ala Ser Trp Asp
                565                 570                 575 gct ttc aat caa ggt gta gaa ggt aat gtc gaa agc gaa gga caa tta       1776
Ala Phe Asn Gln Gly Val Glu Gly Asn Val Glu Ser Glu Gly Gln Leu
            580                 585                 590 gct gac ttt tca att cta ctt act acc tat gct gac aag tac ttc gcc       1824
Ala Asp Phe Ser Ile Leu Leu Thr Thr Tyr Ala Asp Lys Tyr Phe Ala
        595                 600                 605 ata gtc aac aaa gca ttg aag gag cac atg cct aat cat ctg tat ctc       1872
Ile Val Asn Lys Ala Leu Lys Glu His Met Pro Asn His Leu Tyr Leu
```

-continued

```
                610                 615                 620
ggc gct cgt ttt cca gat tgg ggt atg cca att gaa gtg gtt aaa gca      1920
Gly Ala Arg Phe Pro Asp Trp Gly Met Pro Ile Glu Val Val Lys Ala
625                 630                 635                 640 tca gct aaa cat gtc gat gtc att agc ttc aat gta tat aaa gaa ggc      1968
Ser Ala Lys His Val Asp Val Ile Ser Phe Asn Val Tyr Lys Glu Gly
                645                 650                 655 ctt att aaa agc aaa tgg gat ttc tta aaa gag att gac atg cca agc      2016
Leu Ile Lys Ser Lys Trp Asp Phe Leu Lys Glu Ile Asp Met Pro Ser
            660                 665                 670 atc gtt ggc gag tgg cat att ggt gct tcc gat tca ggt ttg ttc cac      2064
Ile Val Gly Glu Trp His Ile Gly Ala Ser Asp Ser Gly Leu Phe His
        675                 680                 685 cct ggc tta att cat gct gcc gat caa gca gac cgc gcc aaa atg tat      2112
Pro Gly Leu Ile His Ala Ala Asp Gln Ala Asp Arg Ala Lys Met Tyr
    690                 695                 700 aaa gac tac atg cat tca gtt atc gac aat gac tat ttt gta ggt gct      2160
Lys Asp Tyr Met His Ser Val Ile Asp Asn Asp Tyr Phe Val Gly Ala
705                 710                 715                 720 cat tgg ttc cag tac atg gac tca cct att acc ggc cga gct tat gat      2208
His Trp Phe Gln Tyr Met Asp Ser Pro Ile Thr Gly Arg Ala Tyr Asp
                725                 730                 735 ggc gag aac tac aat gtc gga ttt att agc gtg act gat cag ccg tac      2256
Gly Glu Asn Tyr Asn Val Gly Phe Ile Ser Val Thr Asp Gln Pro Tyr
            740                 745                 750 aaa ccg att gtt caa gcg gct agc gaa gtc aat gaa gcg atg tat aac      2304
Lys Pro Ile Val Gln Ala Ala Ser Glu Val Asn Glu Ala Met Tyr Asn
        755                 760                 765 aga cgc ttt aaa gcg cag taa                                          2325
Arg Arg Phe Lys Ala Gln
    770
```

<210> SEQ ID NO 2
<211> LENGTH: 774
<212> TYPE: PRT
<213> ORGANISM: Thalassomonas agarivorans

<400> SEQUENCE: 2

```
Met His Asn Lys Met Ser Lys Leu Trp Phe Ala Ser Ala Ile Ser Cys
1               5                   10                  15

Leu Ala Ile Leu Gly Cys Ser Gln Gln Ala Ser Asn Asp Asn Gly
            20                  25                  30

Val Ile Asp Glu Leu Val Asn Phe Ser Ser Gln Thr Thr Leu Asp Gln
        35                  40                  45

Asn Ile Ala Leu Tyr Asn Ala Ser Thr Glu Tyr Asn Ala Glu Thr Arg
    50                  55                  60

Ser Leu Lys Val Asn Phe Asn Thr Ser Glu His Ala Tyr Ser Ser Ile
65                  70                  75                  80

Ser Phe Val Ser Glu Ala Gly Trp Asp Trp Ser Asp Leu Asn Asp Phe
                85                  90                  95

Asn Ile Ala Phe Asp Ile Ala Asn Glu Gly Glu His Ser Thr Gln Val
            100                 105                 110

Tyr Leu Asp Ile Thr Asp Gly Asn Gly Asp Asn Tyr Thr Arg Ser Val
        115                 120                 125

Ser Ile Pro Val Gly Ala Thr Lys Thr Tyr Tyr Ala Lys Met Ala Gly
    130                 135                 140

His Asp Leu Gln Thr Pro Asp Gly Asp Glu Asp Val Glu Leu Asn Phe
145                 150                 155                 160
```

```
Met Ser Gly Leu Arg Ser Asn Pro Asp Thr Trp Gln Ser Asp Glu Val
            165                 170                 175
Asn Phe Ile Ser Leu Trp Gly Lys Lys Asn Leu Asp Val Ser Asn Ile
            180                 185                 190
Lys Arg Ile Ala Phe Ser Val Gln Ser Ala Leu Tyr Asp Lys Ala Ile
            195                 200                 205
Thr Phe Ser Lys Val Gln Ile Arg Gln Asn Pro Ala Met Asp Glu Thr
            210                 215                 220
Phe Leu Thr Gly Ile Val Asp Gln Tyr Gly Gln Asn Ala Lys Gln Glu
225                 230                 235                 240
Phe Val Gly Lys Ile His Asn Asp Gln Glu Leu Leu Ala Ala Arg Asp
            245                 250                 255
Glu Glu Leu Ser Ala Leu Lys Asn Gly Tyr Asp Ala Glu Thr Arg Thr
            260                 265                 270
Lys Phe Gly Gly Trp Lys Asn Gly Pro Arg Gln Glu Ala Thr Gly Tyr
            275                 280                 285
Phe Arg Thr Glu Lys Ile Asn Gly Lys Trp Ser Leu Val Asp Pro Leu
            290                 295                 300
Gly Tyr Pro Tyr Phe Ala Thr Gly Leu Asp Ile Ile Arg Leu Ser Asn
305                 310                 315                 320
Thr Ser Thr Met Thr Gly Tyr Asp Phe Asp Gln Gly Leu Ile Asn Gln
            325                 330                 335
Arg Lys Ala Ser Asp Leu Thr Pro Glu Asp Ser Gln Lys Leu Asn Arg
            340                 345                 350
Val Ser Asn Glu Ala Ala Lys Thr Arg Tyr Val Ala Ser Asp Leu Arg
            355                 360                 365
Lys Asp Leu Phe Thr Trp Leu Pro Ser Tyr Asp Glu Pro Leu Gly Lys
            370                 375                 380
His Tyr Gly Tyr Arg Arg Ser Ala His Ser Gly Pro Leu Ser His Gly
385                 390                 395                 400
Glu Thr Phe Ser Phe Tyr Ser Ala Asn Leu Glu Arg Lys Tyr Ala Asp
            405                 410                 415
Ile Asn Pro Asp Phe Met Glu Val Trp Lys Asp Val Thr Ile Arg Arg
            420                 425                 430
Met Gln Thr Trp Gly Phe Thr Ser Phe Gly Asn Trp Thr Asp Pro Met
            435                 440                 445
Phe Tyr Gln Asn Asp Arg Val Pro Tyr Phe Ala Asn Gly Trp Ile Ile
            450                 455                 460
Gly Asn Tyr Lys Lys Val Ser Ser Gly Asn Asp Phe Trp Ala Pro Leu
465                 470                 475                 480
Pro Asp Val Phe Asp Pro Leu Phe Glu Glu Arg Ala Ile Val Thr Val
            485                 490                 495
Lys Gln Val Ala Ala Glu Val Gln Asn Asn Pro Trp Cys Val Gly Val
            500                 505                 510
Phe Ile Asp Asn Glu Met Ser Phe Gly Arg Pro Asp Ser Val Ala Ser
            515                 520                 525
His Tyr Gly Ile Val Leu Asn Thr Leu Ala Arg Asp Gly Lys Asp Val
            530                 535                 540
Pro Thr Lys Ala Glu Phe Thr Arg Val Met Lys Glu Lys Tyr Gln Asp
545                 550                 555                 560
Ile Ala Ala Leu Asn Lys Ala Trp Gly Thr Asp Ile Ala Ser Trp Asp
            565                 570                 575
```

```
Ala Phe Asn Gln Gly Val Glu Gly Asn Val Glu Ser Glu Gly Gln Leu
            580                 585                 590

Ala Asp Phe Ser Ile Leu Leu Thr Thr Tyr Ala Asp Lys Tyr Phe Ala
            595                 600                 605

Ile Val Asn Lys Ala Leu Lys Glu His Met Pro Asn His Leu Tyr Leu
        610                 615                 620

Gly Ala Arg Phe Pro Asp Trp Gly Met Pro Ile Glu Val Val Lys Ala
625                 630                 635                 640

Ser Ala Lys His Val Asp Val Ile Ser Phe Asn Val Tyr Lys Glu Gly
                645                 650                 655

Leu Ile Lys Ser Lys Trp Asp Phe Leu Lys Glu Ile Asp Met Pro Ser
            660                 665                 670

Ile Val Gly Glu Trp His Ile Gly Ala Ser Asp Ser Gly Leu Phe His
        675                 680                 685

Pro Gly Leu Ile His Ala Ala Asp Gln Ala Asp Arg Ala Lys Met Tyr
    690                 695                 700

Lys Asp Tyr Met His Ser Val Ile Asp Asn Asp Tyr Phe Val Gly Ala
705                 710                 715                 720

His Trp Phe Gln Tyr Met Asp Ser Pro Ile Thr Gly Arg Ala Tyr Asp
                725                 730                 735

Gly Glu Asn Tyr Asn Val Gly Phe Ile Ser Val Thr Asp Gln Pro Tyr
            740                 745                 750

Lys Pro Ile Val Gln Ala Ala Ser Glu Val Asn Glu Ala Met Tyr Asn
        755                 760                 765

Arg Arg Phe Lys Ala Gln
    770

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide primer for amplifying
      agaB1 gene

<400> SEQUENCE: 3
caccatgcat aataaaatga gt                                             22

<210> SEQ ID NO 4
<211> LENGTH: 18
<212> TYPE: DNA
<213> ORGANISM: Artificial Sequence
<220> FEATURE:
<223> OTHER INFORMATION: Synthetic oligonucleotide primer for amplifying
      agaB1 gene

<400> SEQUENCE: 4
ttactgcgct ttaaagcg                                                  18

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide M13 forward primer

<400> SEQUENCE: 5
cgccagggtt ttcccagtca cgac                                           24

<210> SEQ ID NO 6
```

```
-continued

<211> LENGTH: 24
<212> TYPE: DNA
<213> ORGANISM: Artificial Sequence
<220> FEATURE:
<223> OTHER INFORMATION: Synthetic oligonucleotide M13 reverse primer

<400> SEQUENCE: 6
agcggataac aatttcacac agga                                              24
```

β-AGARASE ISOLATED FROM *THALASSOMONAS AGARIVORANS*, PREPARATION PROCESS AND USES THEREOF

FIELD OF THE INVENTION

The present invention relates a β-agarase isolated from *Thalassomonas agarivorans*. The present invention also provides a method for preparing the β-agarase and the uses of the β-agarase.

BACKGROUND OF THE INVENTION

Agar is a linear polysaccharide obtained from the cell wall of some red algae and is composed of agarose and agaropectin. Agarose consists of disaccharide units of 3-O-linked β-D-galactopyranose and 4-O-linked 3,6-anhydro-α-L-galactose. Agarose can be hydrolyzed by agarases. Agarases can be classified into two groups, i.e., α-agarases and β-agarases, according to their enzymatic cleavage sites, as α-agarases cleave the α-1,3 linkage in agarose and β-agarases cleave the β-1,4 linkage in agarose. Agar can be hydrolyzed by acids or α-agarases to obtained agaro-oligosaccharides having a 3,6-anhydro-α-L-galactose group at the reducing end. On the other hand, β-agarases can hydrolyze agar into neoagaro-oligosaccharides having a D-galactose group at the reducing end. Neoagaro-oligosaccharides can only be produced by enzymatic catalysis, not by a chemical method.

β-Agarases can be classified into three glycoside hydrolase families, GH16, GH50 and GH86, on the basis of their amino acid sequences. Most β-agarases belong to family GH16, which can hydrolyze agar and neoagarohexaose and the main product is neoagarotetaose [see Schroeder et. al., (2003) Investigation of the role of a β(1-4) agarase produced by *Pseudoalteromonas gracilis* B9 in eliciting disease symptoms in the red alga *Gracilaria gracilis*. Microbiology 149: 2919-2929, and Allouch et. al., (2003) The three-dimensional structures of two β-agarases. J. Biol. Chem. 278: 47171-47180]. A representative β-agarase in family GH50 is AgaA protein obtained from *Vibrio* sp., which can hydrolyze neoagarotetaose and the main product is neoagarobiose [see Sugano et. al., (1993) Cloning and sequencing of agaA, a unique agarase 0107 gene from a marine bacterium, *Vibrio* sp. strain JT0107. Appl. Environ. Microbiol. 59: 3750-3756]. Representative β-agarases in family GH86 are AgrA protein produced by *Pseudoalteromonas atlantica* T6c [see Belas et. al., (1988) Cloning and gene replacement mutagenesis of a *Pseudomonas atlantica* agarase gene. Appl. Environ. Microbiol. 54: 30-37], and AgaO protein obtained from Microbulbifer-like bacterium, strain JAMB-A94. AgaO can hydrolyze agar and the main end product is neoagarohexaose [see Ohta et. al., (2004) Cloning, expression, and characterization of a glycoside hydrolase family 86 β-agarase from a deep-sea Microbulbifer-like isolate. Appl. Microbiol. Biotechnol. 66: 266-275].

Neoagaro-oligosaccharides have been widely used in food, cosmetic and medical industries. It is found that neoagaro-oligosaccharides can reduce starch decomposition rate and inhibit the growth of bacteria, and thus can be used as low-calorie food additive. In addition, the polysaccharides produced by hydrolyzing marine algae with β-agarases can stimulate the activation of macrophages, and thus can be used as a functional food to enhance immune response [see Yoshizawa et. al., (1995) Macrophage stimulation activity of the polysaccharide fraction from a marine alga (*Porphyra yezoensis*): structure-function relationships and improved solubility. Biosci. Biotechnol. Biochem. 59: 1933-1937]. Furthermore, neoagarobiose produced from β-agarases hydrolysis has skin moisturizing and whitening effects [see Kobayasgu et. al., (1997) Neoagarobiose as a novel moisturizer with whitening effect. Biosci. Biotechnol. Biochem. 61: 162-163]. In molecular biology laboratories, agarases is useful in the purification of DNA by agarose electrophoresis, or in the manufacture of protoplasts of algae [see Araki et. al., (1998) Optimization of parameters for isolation of protoplasts from *Gracilaria verrucosa* (*Rhodophyta*). J. Mar. Biotechnol. 6: 193-197].

However, the activity, stability and yield of the conventional β-agarases produced by the current methods are not satisfying. There is still a need for a new β-agarase with better activity, stability and yield.

*Thalassomonas agarivorans* was isolated by Dr. Shieh Wung Yang's laboratory at National Taiwan University [see Jean et. al., (2006) *Thalassomonas agarivorans* sp. nov., a marine agarolytic bacterium isolated from shallow coastal water of An-Ping Harbour, Taiwan, and emended description of the genus *Thalassomonas*. Int. J. Syst. Evol. Microbiol. 56:1245-1250]. It was found that *Thalassomonas agarivorans* could hydrolyze the agarose in a culture plate, but the type of the agarase produced thereby was unknown. Before Jean et al. (2006), the only strain in the genus *Thalassomonas* known to have agarolytic activity was *Thalassomonas* sp. strain JAMB-A33 [see Hatada et. al., (2006) Hyperproduction and application of α-agarase to enzymatic enhancement of antioxidant activity of porphyran. J. Agric. Food Chem. 54: 9895-9900], and the agarase of *Thalassomonas* sp. strain JAMB-A33 was an α-agarase. Therefore, prior to the invention, no *Thalassomonas* strains was identified to have the ability to produce β-agarase.

SUMMARY OF THE INVENTION

One of the purposes of the present invention is to provide an isolated polypeptide comprising an amino acid sequence selected from the group consisting of:

(a) the amino acid sequence of SEQ ID NO:2;

(b) an amino acid sequence of SEQ ID NO:2 in which one or more amino acids are deleted, substituted and/or added, and having a β-agarase activity; and (c) an amino acid sequence having at least 80% identity to the amino acid sequence of SEQ ID NO:2, and having a β-agarase activity;

or a biologically functional equivalent, derivative or variant thereof.

Another purpose of the present invention is to provide an isolated polynucleotide comprising a nucleotide sequence selected from the group consisting of:

(a) the nucleic acid sequence encoding the polypeptide of the present invention;

(b) the nucleic acid sequence of SEQ ID NO:1;

(c) a nucleic acid sequence having at least 80% identity to the nucleic acid sequence of SEQ ID NO:1, and encoding a polypeptide having a β-agarase activity;

(d) a nucleic acid sequence complementing to any of (a) to (c); and (e) a nucleic acid sequence hybridizing to any of (a) to (d) under highly stringent conditions.

Another purpose of the present invention is to provide an isolated recombinant vector comprising the polynucleotide of the invention.

Another purpose of the present invention is to provide an isolated recombinant host cell comprising the vector of the invention.

Another purpose of the present invention is to provide a method of producing the polypeptide of the invention comprising:
(a) incubating the host cell of the invention under conditions suitable for expression of the polypeptide; and
(b) isolating the polypeptide from the host cell and/or host cell culture.

Another purpose of the present invention is to provide a method of extracting a material from agarose gel comprising:
(a) hydrolyzing the agarose gel containing the material with the polypeptide of the invention; and
(b) isolating the material from the hydrolysate and purifying the same.

Still another purpose of the present invention is to provide a method of producing neoagaro-oligosaccharides (e.g., neoagarotetraose, neoagarohexaose and neoagarobiose) comprising hydrolyzing agar, agarose, neoagarohexaose, neoagarotetraose, or the mixture thereof with the polypeptide of the invention.

A further purpose of the present invention is to provide a kit comprising the polypeptide of the invention and one or more reagents for isolating nucleic acid.

The present invention is described in detail in the following sections. Other characteristics, purposes and advantages of the present invention can be easily found in the detailed descriptions and claims of the invention.

DETAILED DESCRIPTION OF THE INVENTION

Figure 1A:
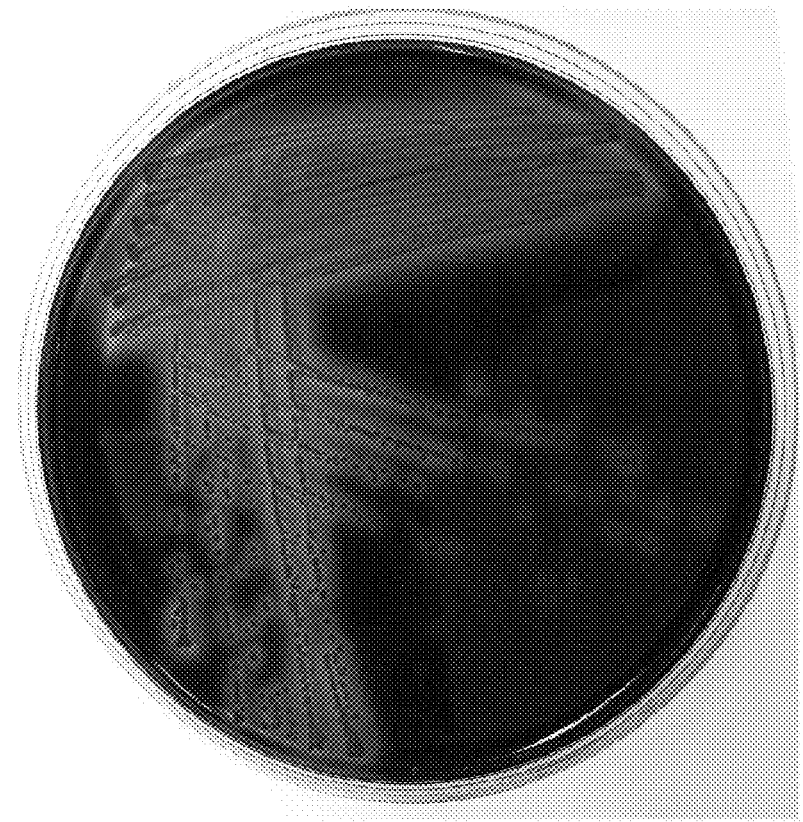
FIG. 1A shows the growth of pcc1clone A clone on the culture plate (left) and the results of Gram's iodine reagent staining on the plate (right).
Figure 1A:
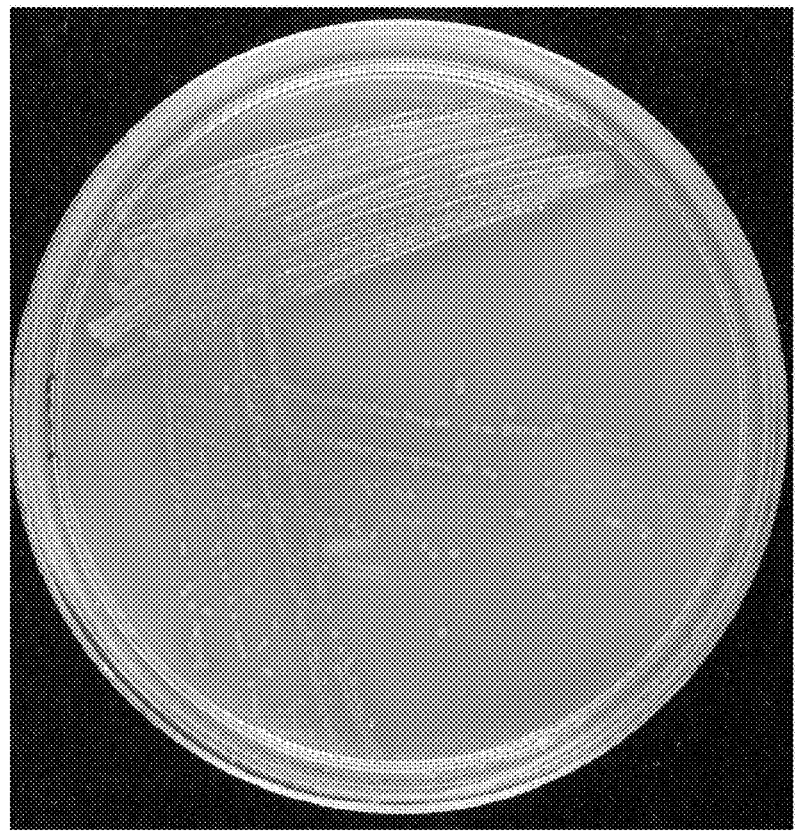

A novel agarase gene, named agaB1, was cloned from *Thalassomonas agarivorans* (BCRC 17492, JCM 13379). It is found that the sequence of agaB1 is different from that of the α-agarase gene agaA33 (GenBank Accession No. AB211981) from *Thalassomonas* sp. strain JAMB-A33 discovered by Hatada et. al. [see Hatada et. al (2006) Hyperproduction and application of α-agarase to enzymatic enhancement of antioxidant activity of porphyran. *J. Agric. Food Chem.* 54: 9895-9900]. Upon comparison, it is found that agaB1 encodes a β-agarase belonging to family GH50.

DEFINITIONS

Unless otherwise defined herein, scientific and technical terms used in connection with the present invention shall have the meanings that are commonly understood by those of ordinary skill in the art. The meaning and scope of the terms should be clear. However, in the event of any latent ambiguity, definitions provided herein take precedent over any dictionary or extrinsic definition.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "isolated polypeptide" referred to herein means that a subject polypeptide (1) is free of at least some other polypeptides with which it would normally be found, (2) is essentially free of other polypeptides from the same source, e.g., from the same species, (3) is expressed by a cell from a different species, (4) is separated from at least about 50 percent of polynucleotides, lipids, carbohydrates, or other materials with which it is associated in nature, (5) is not associated (by covalent or non-covalent interaction) with portions of a polypeptide with which the isolated polypeptide is associated in nature, (6) is operably associated (by covalent or non-covalent interaction) with a polypeptide with which it is not associated in nature, or (7) does not occur in nature. Genomic DNA, cDNA, mRNA or other RNA of synthetic origin, or any combination thereof may encode such an isolated polypeptide. Preferably, the isolated polypeptide is substantially free from polypeptides or other contaminants that are found in its natural environment and that would interfere with its research or other use. An isolated polypeptide may also be rendered substantially free of naturally associated components by isolation, using protein purification techniques well known in the art.

The term "amino acid sequence" means an amino acid sequence of a naturally occurring protein molecule. "Amino acid sequence" and the similar terms, such as "polypeptide" or "protein," are not meant to limit the amino acid sequence to the complete, native amino acid sequence associated with the recited protein molecule. Amino acid sequence includes an oligopeptide, peptide, polypeptide, or protein sequence, and fragments or portions thereof, and to naturally occurring or synthetic molecules.

The term "biologically functional equivalent" refers to equivalents with respect to the polypeptide of the present invention that contain a sequence or moiety exhibiting sequence similarity to the novel polypeptides of the present invention, and that exhibit the same or similar functional properties as that of the polypeptides disclosed herein, i.e., agarase activity. For instance, the biologically functional equivalent of the polypeptide of the invention may have some alterations in the amino acid sequence that is different from, but essentially identical to, the amino acid sequence of the polypeptide, and has essentially identical properties of the polypeptide as described herein, even if of a lesser or greater degree.

The terms "derivatives" and "variants" of proteins, polypeptides, and peptides according to the invention are described in terms of differences from proteins and/or polypeptides and/or peptides according to the invention, meaning that the derivatives and variants, which are proteins/polypeptides/peptides according to the invention, differ from underivatized or non-variant proteins, polypeptides or peptides of the invention in the manner defined. One of skill in the art would understand that the derivatives and variants themselves are proteins, polypeptides and peptides according to the invention.

The terms "isolated polynucleotide" referred to herein means that a subject polynucleotide (1) is not associated (covalently or non-covalently) with all or a portion of other polynucleotides with which the subject polynucleotide is associated in nature, (2) is not associated with a molecule with which it is not associated in nature, or (3) does not occur in nature associated with any other polynucleotides. Such a polynucleotide may be genomic DNA, cDNA, mRNA or other RNA of synthetic origin, or any combination thereof. Preferably, the isolated and purified polynucleotide of the invention comprises a single coding region. Although the polynucleotide includes a single coding region, it can contain additional nucleotides that do not detrimentally affect the function of the polynucleotide. For example, the 5' and 3' untranslated regions may contain variable numbers of nucleotides. Preferably, additional nucleotides are outside the single coding region.

The term "nucleic acid sequence" means single-stranded or double-stranded nucleic acid polymers of at least 10 bases in length. In certain embodiments, the nucleotides comprising the polynucleotide can be ribonucleotides or deoxyribonucleotides or a modified form of either type of nucleotide. Said modifications include base modification such as bromouridine and inosine derivatives, ribose modification such as 2',3'-dideoxyribose, and internucleotide linkage modifications such as phosphorodiselenoate, phosphoroanilothioate, phosphoranilidate and phosphoroamidate, and the like. A nucleic acid sequence of the invention can include a label, including a radiolabel, a fluorescent label, a hapten or an antigenic label for detection assays.

The term "vector" means any molecule (e.g., nucleic acid, plasmid, episome, or virus) used to transfer coding information to a host cell. The term also includes a "recombinant vector," "expression vector" or "expression construct." The term "expression vector" or "expression construct" refers to a vector that is suitable for transformation of a host cell and contains nucleotide sequences that direct and/or control (in conjunction with the host cell) expression of one or more heterologous coding regions operatively linked thereto. An expression construct may include, but is not limited to, sequences that affect or control transcription, translation, and RNA splicing, if introns are present, of a coding region operatively linked thereto. Preferred vectors are those capable of autonomous replication and expression of nucleic acids to which they are linked.

The term "host cell" means a cell that has been transformed, or is capable of being transformed, with a nucleic acid sequence and thereby expresses a selected gene of interest. The term includes the progeny of the parent cell, whether or not the progeny is identical in morphology or in genetic mark-up to the original parent cell, so long as the selected gene is present.

The term "transformation" refers to a change in a cell's genetic characteristics, and a cell is transformed when it is modified to contain new DNA. For example, a cell is transformed where it is genetically modified from its native state by transfect, transduction, or other techniques.

The term "identity" refers to a relationship between the sequences of two or more polypeptide molecules or two or more nucleic acid molecules, as determined by comparing the sequences thereof. "Identity" measures the percentage of identical matches between the smaller of two or more sequences.

The term "similarity" is used in the art with regard to a related concept; in contrast to "identity," however, "similarity" refers to a measure of relatedness that includes both identical matches and conservative substitution matches.

Unless otherwise required by context, singular terms shall include the plural and plural terms shall include the singular.

β-Agarase and Gene Thereof

In certain embodiments of the invention, there is an isolated polypeptide comprising an amino acid sequence selected from the group consisting of:
   (a) the amino acid sequence of SEQ ID NO:2;
   (b) an amino acid sequence of SEQ ID NO:2 in which one or more amino acids are deleted, substituted and/or added, and having a β-agarase activity; and
   (c) an amino acid sequence having at least 80% identity to the amino acid sequence of SEQ ID NO:2, and having a β-agarase activity;
or a biologically functional equivalent, derivative or variant thereof.

In a preferred embodiment of the invention, there is a polypeptide comprising the amino acid sequence of SEQ ID NO:2, which is a β-agarase having the following physicochemical properties (a) to (e):
   (a) a molecular weight of about 87.6 kDa;
   (b) an optimum reaction temperature of about 35 to 40° C.;
   (c) an optimum reaction NaCl concentration of about 150 to 200 mM;
   (d) an optimum reaction pH of about pH 7 to 8; and
   (e) an activity on hydrolyzing agarose into neoagaro-oligosaccharides, mainly neoagarobiose, but not λ-carrageenan, κ-carrageenan or ι-carrageenan.

Peptides, polypeptides, proteins biologically functionally equivalent, derivatives and variants of the protein of the invention are contemplated as within the scope of the invention and include amino acid sequences containing conservative amino acid changes in the fundamental sequence of the protein. In such amino acid sequences, one or more amino acids in the fundamental sequence are substituted with another amino acid(s), the charge and polarity of which are similar to that of the native amino acid, i.e., a conservative amino acid substitution, resulting in a silent change. Substitutes for an amino acid within the fundamental polypeptide sequence can be selected from other members of the class to which the naturally occurring amino acid belongs.

Amino acids can be divided into the four following groups: (1) acidic amino acids, (2) basic amino acids, (3) neutral polar amino acids, and (4) neutral nonpolar amino acids. Representative amino acids within these various groups include, but are not limited to, (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; (4) neutral nonpolar (hydrophobic) amino acids such as alanine, leucine, isoleucine, valine, proline, phenylalanine, tryptophan, and methionine.

Combinations of the foregoing, i.e., forms of the polypeptides containing both amino acid deletions and additions, are also encompassed by the present invention. Amino acid substitutions can also be present.

Biologically functional equivalent, derivatives and variants peptides, polypeptides, and proteins contemplated herein should therefore possess about 80% or greater sequence identity, preferably about 85% or greater sequence identity, and most preferably about 90% or greater sequence identity, e.g., 95%, to the sequence of, or corresponding moiety within, the fundamental amino acid sequence of polypeptide of the invention. The biologically functional equivalents of the protein can have 20 or fewer conservative amino acid changes, more preferably 10 or fewer conservative amino acid changes, and most preferably five or fewer conservative amino acid changes. The encoding nucleotide sequence (gene, plasmid DNA, cDNA, or synthetic DNA) will thus have corresponding base substitutions, permitting it to encode biologically functional equivalent forms of the protein.

Biologically functional equivalents, derivatives or variants also include peptides, polypeptides, and proteins that react with, i.e., specifically bind to, antibodies raised against the protein of the invention and that exhibit the same or similar β-agarase activity, including both monoclonal and polyclonal antibodies Methods for altering the amino acid sequences are well known in the art, such as genetic engineering techniques, e.g., site-directed mutagenesis to modify the nucleotide acid sequences or the amino acid sequences and expression of recombinant proteins.

More specifically, the polypeptide is produced as follows: recombinant DNA (expression vector) which enables expression of a gene encoding the desired protein in a host cell is prepared; the DNA is introduced into the host cell to thereby transform the cell; the resultant transformant is cultivated; and the protein is recovered from the cultivated products.

The invention also provides polynucleotides (isolated or purified or pure polynucleotides) encoding the proteins or peptides according to the invention, vectors (including cloning vectors and expression vectors) comprising such polynucleotides, and cells (e.g., host cells) transformed or transfected with a polynucleotide or vector according to the invention. In certain embodiments of the invention, there is an isolated polynucleotide comprising a nucleotide sequence selected from the group consisting of:
   (a) the nucleic acid sequence encoding the polypeptide of the invention;
   (b) the nucleic acid sequence of SEQ ID NO:1;
   (c) a nucleic acid sequence having at least 80% identity to the nucleic acid sequence of SEQ ID NO:1, and encoding a polypeptide having a β-agarase activity;
   (d) a nucleic acid sequence complementing any of (a) to (c); and
   (e) a nucleic acid sequence hybridizing to any of (a) to (d) under highly stringent conditions.

Preferably, the polynucleotide comprises the nucleic acid sequence of SEQ ID NO:1.

Due to the degeneracy of the genetic code, i.e., the existence of more than one codon for most of the amino acids naturally occurring in proteins, other DNA (and RNA) sequences that contain essentially the same genetic information as the DNA of the present invention and that encode substantially the same amino acid sequence as that encoded by the nucleotide sequence of SEQ ID NO:1, can be used to practice the present invention. This principle applies as well to any of the other nucleotide sequences discussed herein.

The present invention includes not only the nucleic acid sequence shown in SEQ ID NO:1 but also biologically functional equivalent nucleic acid sequences. The phrase "biologically functional equivalent nucleic acid sequences" denotes DNAs and RNAs, including genomic DNA, plasmid DNA, cDNA, synthetic DNA, and mRNA nucleotide sequences that encode peptides, polypeptides, and proteins exhibiting the same or similar activity as that of SEQ ID NO:2, i.e., when introduced into host cells in a functionally operable manner so that they are expressed, they produce peptides, polypeptides, or proteins exhibiting β-agarase activity.

In addition to nucleic acid sequences encoding conservative amino acid changes within the fundamental polypeptide sequence, biologically functional equivalent nucleic acid sequences of the present invention include nucleic acid sequences containing other base substitutions, additions, and/or deletions. These include nucleic acids containing the same inherent genetic information as that contained in the DNA of SEQ ID NO:1, and which encode peptides, polypeptides, or proteins having β-agarase activity the same as or similar to that of SEQ ID NO:2. Such nucleic acid sequences can be referred to as "genetically equivalent modified forms" of the DNA shown in SEQ ID NO:1 and can be identified by the methods described herein.

Mutations made in the cDNA, plasmid DNA, genomic DNA, synthetic DNA, or other nucleic acids encoding a polypeptide of the invention, such as SEQ ID NO:1, preferably preserve the reading frame of the coding sequence. Furthermore, these mutations preferably do not create complementary regions that could hybridize to produce secondary mRNA structures, such as loops or hairpins, that would adversely affect mRNA translation.

Although mutation sites can be predetermined, the nature of the mutations per se need not be predetermined. For example, in order to select for optimum characteristics of mutants at a given site, random mutagenesis can be conducted at the target codon. Alternatively, mutations can be introduced at particular loci by synthesizing oligonucleotides containing a mutant sequence, flanked by restriction sites enabling ligation to fragments of the native cDNA sequence. Following ligation, the resulting reconstructed nucleic acid sequence encodes a derivative form of the polypeptide sequence having the desired amino acid insertion, substitution, or deletion. In either case, the expressed mutants can be screened for desired β-agarase activity, for example, with the method described in Examples 1 and 7.

Specific examples of useful genetically equivalent modified forms of the nucleic acid sequence of SEQ ID NO:1 include polynucleotide having a nucleic acid sequence that exhibits a high level of sequence identity to SEQ ID NO:1. Variant polynucleotides are at least 75%, and preferably 80%, 85%, 90%, 95% or 99% identical to one of the polynucleotides of defined sequence as described herein, or hybridize to one of those polynucleotides of defined sequence under stringent hybridization conditions of 0.015 M sodium chloride, 0.0015 M sodium citrate at 65-68° C. or 0.015 M sodium chloride, 0.0015M sodium citrate, and 50% formamide at 42° C. The polynucleotide variants retain the capacity to encode a protein of the invention.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., Molecular Cloning: A Laboratory Manual, 2nd Ed., Cold Spring Harbor Laboratory (Cold Spring Harbor, N.Y. 1989).

More stringent conditions (such as higher temperature, lower ionic strength, higher formamide, or other denaturing agent) may also be used; however, the rate of hybridization will be affected. In instances which concern hybridization of deoxyoligonucleotides, additional exemplary stringent hybridization conditions include washing in 6×SSC, 0.05% sodium pyrophosphate at 37° C. (for 14-base oligonucleotides), 48° C. (for 17-base oligonucleotides), 55° C. (for 20-base oligonucleotides), and 60° C. (for 23-base oligonucleotides).

The polynucleotide of the invention is preferably obtained by means of a DNA/RNA amplification method employing PCR [see Science, 230, 1350 (1985)]. Primers employed in such PCR are appropriately designed on the basis of sequence information of the polynucleotide of the invention, such as SEQ ID NO:1, and can be synthesized by means of a customary method. Examples of the primer include a primer containing a partial nucleic acid sequence of the polynucleotide of the invention and having usually about 10 to 35 nucleotides, preferably about 15 to 30 nucleotides. Isolation and purification of amplified DNA/RNA fragments can be carried out through a conventional method, for example, through gel electrophoresis.

Vector and Host System

Another object of the invention is to provide a vector containing the polynucleotide of the invention. In order to express a biologically active protein of the invention, the nucleotide sequence encoding the protein of the invention or biologically functional equivalents may be inserted into an appropriate expression vector, i.e., a vector which contains the necessary elements for the transcription and translation of the inserted coding sequence. According to the invention, methods well known to those skilled in the art may be used to construct expression vectors containing sequences encoding the protein of the invention and appropriate transcriptional and translational control elements. These methods include in vitro recombinant DNA techniques, synthetic techniques, and in vivo genetic recombination. The vector is typically selected to be functional in the particular host cell employed (i.e., the vector is compatible with the host cell machinery so that amplification of the gene and/or expression of the gene can occur).

Another object of the invention is to provide a host cell transformed with the polynucleotide sequence of the invention or the vector containing the sequence. According to the invention, a number of host systems may be utilized to contain and express sequences encoding the protein of the invention. These include, but are not limited to, microorganisms such as bacteria transformed with recombinant bacteriophage, plasmid, or cosmid DNA expression vectors; yeast transformed with yeast expression vectors; insect cell systems infected with virus expression vectors; plant cell systems transformed with virus expression vectors or with bacterial expression vectors; or animal cell systems. After the vector is constructed and a polynucleotide sequence encoding the protein of the invention is inserted into the proper site of the vector, the completed vector may be inserted into a suitable host cell for amplification and/or polypeptide expression.

Examples of the prokaryotic host cells include widely used *Escherichia coli* and *Bacillus subtilis*. Preferably, *Escherichia coli* is used. Examples of the eukaryotic host cells include vertebrate cells and yeast cells. Preferred examples of the vertebrate cells include monkey COS cell [see Gluzman Y., (1981) SV40-transformed simian cells support the replication of early SV40 mutants. Cell, 23: 175-182], Chinese hamster ovarian cell, and dihydrofolic-acid-reductase-defective cell strain of the ovarian cell [see Urlaub et. al., (1980) Isolation of Chinese hamster cell mutants deficient in dihydrofolate reductase activity. Proc Natl Acad Sci USA. 77(7): 4216-4220]. Preferred examples of the yeast cells include *Saccharomyces* cells. The host cell is not limited to the above examples.

When a prokaryotic cell is used as a host, a vector which can be replicated in the host cell is used. Examples of preferred vectors include an expression plasmid containing a promoter at an upstream position of the gene of the present invention, an SD (Shine-Dalgarno) sequence, and an initiation codon (e.g., ATG) necessary for initiation of protein synthesis, so that the gene can be expressed in the host cell. In general, an *Escherichia coli*-derived plasmid, such as pBR322, pBR325, pUC12, pUC13, pUC19, pEZseq or pCC1 is widely used as the aforementioned vector. The vector is not limited to these examples, and a variety of known vectors may be used. Examples of commercially available *Escherichia coli*-derived vectors used for expression of the gene include CopyControl™ pCC1 vector (Epicentre).

Examples of expression vectors used when a vertebrate cell is used as a host include a vector containing a promoter located at an upstream position of the gene of the present invention which is to be expressed, a splice site of RNA, a polyadenylation site, and a transcription termination sequence. If necessary, the vector may contain a replication origin. Specific examples of the expression vector include pSV2dhfr having an initial promoter of SV40 [Subramani et al., (1981) Expression of the mouse dihydrofolate reductase complementary deoxyribonucleic acid in simian virus 40 vectors. Mol. Cell. Biol., 1: 854-864]. In addition, a variety of commercially available known vectors can be used. Examples of commercially available vertebrate-cell-derived vectors used for expression of the gene include animal cell vectors, such as pEGFP-N and pEGFP-C (products of Clontech), pIND (product of Invitrogen), and pcDNA3.1/His (product of Invitrogen); and insect cell vectors, such as pFastBac HT (product of GibcoBRL), pAcGHLT (product of PharMingen), and pAc5/V5-His, pMT/V5-His, and pMT/Bip/V5-his (products of Invitrogen).

Specific examples of expression vectors used when a yeast cell is used as a host include pAM82 having a promoter corresponding to an acidic phosphatase gene [see Miyanohara et al., (1983) Expression of hepatitis B surface antigen gene in yeast. Proc. Natl. Acad. Sci., USA., 80(1): 1-5]. Examples of commercially available yeast cell expression vectors include pPICZ and pPICZ[alpha] (products of Invitrogen).

The type of the promoter employed is not particularly limited. For example, when *Escherichia* bacteria are used as a host, a tryptophan (trp) promoter, an lpp promoter, an lac promoter, an recA promoter, or a PL/PR promoter is preferably used. When *Bacillus* bacteria are used as a host, for example, an SP01 promoter, an SP02 promoter, or a penP promoter is preferably used. When yeast is used as a host, for example, a pH05 promoter, a PGK promoter, a GAP promoter, or an ADH promoter is preferably used. When an animal cell is used as a host, for example, an SV40-derived promoter, a retrovirus promoter, a metallothionein promoter, a heat shock promoter, a site megalovirus promoter, or an SR[alpha] promoter is preferably used.

No particular limitation is imposed on the method for introducing desired recombinant polynucleotide (or vector) into a host cell and transforming the host cell. The transformation of an expression vector comprising the polynucleotide of the invention into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. The host cell, when cultivated under appropriate conditions, may synthesize the protein of the invention that can subsequently be collected from the culture medium (if the host cell secretes it into the medium) or directly from the host cell producing it (if it is not secreted). The selection of an appropriate host cell will depend upon various factors such as desired expression levels, polypeptide modifications that are desirable or necessary for activity (such as glycosylation or phosphorylation) and ease of folding into a biologically active molecule.

The thus-obtained transformant can be cultivated by means of a customary method. Through cultivation, the target polypeptide of the present invention encoded by the desirably designed gene is expressed and produced (accumulated and secreted) inside or outside the cells of the transformant, or on the plasma membrane of the transformant.

In accordance with the host cell employed, the medium used for the culture may be selected from a variety of conventionally used media. The cultivation may be carried out under conditions suitable for growth of the host cell.

If desired, the thus-obtained recombinant polypeptide of the present invention may be subjected to separation and purification through a variety of separation techniques making use of physical and chemical properties of the protein [see "Biochemistry Data Book II," pp. 1175-1259, first edition, first printing, Jun. 23, 1980, published by Tokyo Kagaku Dojin; Arakawa et al., (1986) Structure of unfolded and refolded recombinant derived [Ala125]interleukin 2. Biochemistry, 25 (25): 8274-8277; and Langley et al., (1987) Recombinant-DNA-derived bovine growth hormone from *Escherichia coli* 1. Demonstration that the hormone is expressed in reduced form, and isolation of the hormone in oxidized, native form. Eur. J. Biochem. 163: 313-21].

Specific examples of the separation technique include usual reconstruction treatment, treatment by use of a protein precipitant (salting-out), centrifugation, an osmotic pressure shock method, sonication, ultrafiltration, molecular sieve chromatography (gel filtration), adsorption chromatography, ion-exchange chromatography, affinity chromatography, high performance liquid chromatography (HPLC), dialysis, and combinations thereof. More preferably, affinity chromatography employing a column bound to an antibody specific to the polypeptide of the present invention is carried out.

Utility

Because the polypeptide of the invention is a β-agarase capable of hydrolyzing the agarose in the agar composition, the polypeptide of the invention is applicable to the extraction of a desired material from agarose gel. For example, a DNA or RNA fragment in an objective region, which is preliminarily identified by agarose electrophoresis, can be readily extracted by hydrolyzing the agar around the region with the polypeptide of the invention.

The polypeptide of the invention may be presented in the form of a kit. The kit of the invention may comprise the polypeptide of the invention and one or more reagents for isolating and/or purifying the nucleic acid sample (a DNA or RNA sample) from hydrolyzed agarose, which are well known to those skilled in the art. The kit may further comprise written instructions for isolating and/or purifying the nucleic acid sample from agarose. Examples include, but are not limited to, various containers (e.g., bottles, cartons, blister packs, and ampoules) either accompanied by a package insert describing the detecting instructions, or wherein the instructions are printed on or affixed to the container.

Another functionality of polypeptide of the invention is cleavage of agar, agarose, neoagarohexaose or neoagarotetraose to generate neoagaro-oligosaccharides. Thus, the polypeptide of the invention can be used in the production of neoagaro-oligosaccharides, such as neoagarobiose.

The following examples are provided to aid those skilled in the art in practicing the present invention. Even so, the examples should not be construed to unduly limit the present invention as modifications and variations in the embodiments discussed herein may be made by those having ordinary skill in the art without departing from the spirit or scope of the present inventive discovery.

EXAMPLES

Example 1

Extraction of *T. agarivorans* Chromosomal DNA

*Thalassomonas agarivorans* is publicly available from the Bioresource Collection and Research Center (BCRC; 331, Shir-Pin Rd., Hsinchu 30062, Taiwan, ROC) under deposit number BCRC 17492 and from the Japan Collection of Microorganisms (JCM, 2-1 Hirosawa, Wako, Saitama 351-0198, Japan) under deposit number JCM 13379. The optimum growth temperature of *T. agarivorans* is about 26° C. and it was found that said strain could decompose agar in the culture medium.

*T. agarivorans* strain was cultivated by shaking in 100 ml of BCRC medium 615 (Polypepton-Yeast (PY) broth medium containing 2 g polypepton, 0.5 g bacto-yeast extract, 30 g NaCl, 5 g $MgCl_2.6H_2O$, 0.005 g $CaCl_2$, 0.005 g $Na_2MoO_4.7H_2O$, 0.004 g $CuCl_2.2H_2O$, 0.006 g $FeCl_3.6H_2O$ and 6 g Tris per liter; 1.5% agar could be added if needed; adjusted to pH 8.0 before autoclave) at 26° C. for 3 days. The culture was centrifuged at 4,500 rpm for 20 minutes. The supernatant was discarded and the bacterial cells were collected.

The cells were re-suspended in 11 ml of B1 buffer (50 mM Tris-HCl, pH 8.0; 50 mM EDTA, pH 8.0; 0.5% Tween-20; 0.5% Triton X-100), and then 30 mg of lysozyme and 110 µl of RNase (20 mg/ml) were added thereto. After incubation at 37° C. for 1 hour, 10 mg of proteinase K and 110 mg of sodium lauroyl sarcosine (Amresco Co.) were added thereto and the solution was then incubated at 50° C. for 2 hours. Tris saturated phenol was added to the solution in a 1:1 (v/v) ratio and they were mixed on a rotating plate for 10 minutes. The mixed solution was centrifuged at 3,500 rpm at room temperature for 30 minutes, and the supernatant was collected. The steps of the addition of Tris saturated phenol deproteinization, mixing, centrifugation and collection were repeated twice. The collected solution was extracted with a same volume of chloroform, and the supernatant was taken out and mixed with a same volume of isopropanol on a rotating plate for 10 minutes. The chromosomal DNA in filamentous form was collected by a plastic inoculating loop. The chromosomal DNA was washed with 70% alcohol and dried in the air at room temperature.

To determine the concentration of DNA, the dried chromosomal DNA was dissolved in sterile water and then analyzed by agarose electrophoresis and Nanodrop (NanoDrop Technologies).

Example 2

Cloning of *T. agarivorans* Agarase Gene

To construct a genomic DNA shotgun library of *T. agarivorans*, the chromosomal DNA obtained from Example 1 was sheared by Hydroshear® DNA Shearer (BST Scientific) to DNA fragments having sizes between 1 to 5 kb. The DNA fragments were fractionated by agarose gel electrophoresis and the portions of gel containing the DNA fragments that had the sizes between 2 to 4 kb were cut off, and the DNA fragments contained therein were purified with a gel purification kit (Geneaid Co.). Each purified DNA fragment was end-repaired and cloned into the vector CopyControl™ pCC1™ (Epicentre), and the vector was transformed into *E. coli* competent cell TransforMax™ EPI300™ (Epicentre).

The recombinant *E. coli* clones were inoculated onto the culture plates with LB medium (containing 0.01% arabinose, 0.4 mM IPTG and 12.5 µg/ml chloramphenical). After incubation at 37° C. overnight, the plates were kept at room temperature for 10 days and the hydrolysis of agar in the medium caused by the production of agarase was observed. A clone, named pcc1clone A, was found to have the ability to hydrolyze agar in the medium. The clone pcc1clone A was then inoculated onto a plate with LB medium (containing 0.01% arabinose, 0.4 mM IPTG and 12.5 µg/ml chloramphenical) and incubated at 37° C. for 24 hours. The plate was stained with Gram's iodine reagent (0.05 M $I_2$ dissolved in 0.12 M KI), and the light yellow clear zones shown in the plate prove that pcc1clone A is capable of producing agarase (see FIG. 1A).

Example 3

DNA Sequencing of the Agarase

The plasmid obtained from pcc1clone A was digested with BamH1, and an insertion DNA fragment having a size of about 4.4 kb was obtained. This DNA fragment was purified, and then sheared by Hydroshear® DNA Shearer. The resulting fragments were separated by agarose gel electrophoresis and the portions of the gel containing the DNA fragments that had the sizes between 0.75 to 1.0 kb were cut off, and the DNA fragments contained therein were purified. Each purified DNA fragment was ligated into the cloning vector pEZSeq Amp utilizing pEZSeq™ Amp Blunt Cloning Kit (Lucigen Co.) and the recombinant vector was transformed into *E. coli* competent cell TransforMax™ EPI300™.

The recombinant *E. coli* clones were inoculated onto culture plates with LB medium containing 100 µg/ml ampicillin, 0.4 mM IPTG and 90 µg/ml X-Gal. After incubation at 37° C. overnight, 46 white colonies were selected. Each colony was inoculated into 1 ml LB culture broth (comprising 100 µg/ml Ampicillin) and incubated at 37° C. overnight. The plasmid DNA of each colony was isolated by using alkaline lysis and sequenced by using BigDye® Terminator v3.1 Cycle Sequencing Kits (Applied Biosystem). The sequencing was carried out with the utilization of the sequencing primers Z-For (M13 Forward) 5'-CGCCAGGGTTTTCCCAGT-CACGAC-3' (SEQ ID NO: 5) and Z-Rev (M13 Reverse) 5'-AGCGGATAACAATTTCACACAGGA-3' (SEQ ID NO: 6), and analyzed by ABI 3730 Sequencer (Applied Biosystem).

92 sequences were obtained and assembled by the assembling program, ContigExpress, of the Vector NTI (Invitrogen Co.) software to obtain an assembled sequence having 4,434 bp. The assembled sequence was analyzed by utilizing an ORF finder software available on NCBI's website (http://www.ncbi.nlm.nih.gov/gorf/gorf.html) to find the open reading frame (ORF). The ORF found was analyzed by utilizing a blastx program available on NCBI's website (http://www.ncbi.nlm.nih.gov/BLAST/). It is found that the sequence is a novel β-agarase gene having 2,325 bp (SEQ ID NO:1) and is named agaB1. The agaB1 gene encodes a protein AgaB1 (SEQ ID NO:2) having 774 amino acids. The predicted molecular weight of this protein is 87,613 Da and the predicted isoelectric point is pH 5.05.

Example 4

Sequence Comparison Analysis of AgaB1

The DNA sequence of agaB1 (SEQ ID NO:1) was blasted against the non-redundant nucleotide sequence database (nr/nt etc.) at NCBI using the blastn program. The program selection is for "somewhat similar sequence." The results of the Blast search are provided in Table 1. It is found that the agarase genes that are most similar to agaB1 gene are those of *Pseudoalteromonas atlantica* T6c (GenBank Accession Nos. ABG40489.1 and ABG41155.1) and the similarity is 73%. The fact that the highest similarity of agaB1 gene to other agarase genes is only 73% confirms that agaB1 gene found in *T. agarivorans* is a novel agarase gene.

The amino acid sequence translated from agaB1 gene (AgaB1; SEQ ID NO:2) was blasted against the non-redundant protein sequence database (nr etc.) at NCBI using the blastp program. The results of the Blast search are provided in Table 2. It is found that AgaB1 has a similarity of 63% to the β-agarase of *Pseudoalteromonas atlantica* T6c (GenBank Accession No. ABG40489.1), a similarity of 57% to the β-agarase of *Alteromonas* sp. E-1 (GenBank Accession No. BAE97587.1) and a similarity of 58% to the β-agarase of *Saccharophagus degradans* 2-40 (GenBank Accession No. ABD81904.1). The fact that the highest similarity of AgaB1 to other agarases is only 63% further confirms that AgaB1 found in *T. agarivorans* is a novel agarase.

Example 5

Construction of Expression Vector

To amplify the full length ORF of agaB1, the plasmid DNA of pcc1clone A is used as the PCR template, and the forward primer is 5'-CACCATGCATAATAAAATGAGT-3' (SEQ ID NO: 3; the underlined sequence is designed for the ligation with pET151/D-TOPO plasmid) and the reverse primer is 5'-TTACTGCGCTTTAAAGCG-3' (SEQ ID NO: 4). The PCR reaction solution comprises 250 ng of pcc1clone A plasmid DNA, 8 μl of 2.5 mM dNTP, 10 μl of 10×PCR buffer, 2 μl of 10 μM forward primer and reverse primer, and 5 U Taq enzyme (Takara Co.). The total volume of the reaction solution is 100 μl and the PCR conditions are (1) 95° C. for 5 minutes; (2) 95° C. for 30 seconds, 50° C. for 30 seconds and 72° C. for 2 minutes per cycle of a total of 30 cycles; (3) 72° C. for 10 minutes; and (4) maintained at 4° C. AgaB1 gene was obtained by agarose electrophoresis and purified by a gel purification kit (Geneaid Co.). The purified agaB1 gene was ligated with pET151/D-TOPO vector (Invitrogen Co.) and then transformed into *E. coli* strain Top10 (Invitrogen Co.).

The recombinant *E. coli* clones were inoculated onto LB plates (comprising 100 μg ampicillin) and incubated at 37° C. overnight. 6 clones were selected and incubated in 3 ml of LB broth (containing 100 μg/ml Ampicillin) at 37° C. overnight.

TABLE 1

Comparison analysis (blastn) of the DNA sequence of agaB gene

| Accession | Description | Max score | Total score | Query coverage | E value | Max identities | Protein ID |
|---|---|---|---|---|---|---|---|
| AY212800.1 | Uncultured bacterium clone XIVA3, complete cds | 410 | 762 | 60% | 1e-110 | 69% | |
| AY236225.1 | Uncultured bacterium cosmid IIIE5_0426 sequence | 410 | 762 | 60% | 1e-110 | 69% | |
| AB198068.1 | *Alteromonas* sp. E-1 gene for beta-agarase, complete cds | 405 | 505 | 55% | 5e-109 | 72% | BAE97587.1 beta-agarase |
| AY236223.1 | Uncultured bacterium cosmid XB11 sequence | 405 | 757 | 57% | 5e-109 | 70% | |
| CP000388.1 | *Pseudoalteromonas atlantica* T6c, complete genome | 228 | 789 | 65% | 8e-56 | 73% | ABG40489.1 agarase ABG41155.1 agarase |
| CP000282.1 | Saccharophagus degradans 2-40, complete genome | 201 | 780 | 55% | 1e-47 | 70% | ABD81904.1 beta-agarase ABD80438.1 beta-agarase |
| AY212801.1 | Uncultured bacterium clone VIIC10 | 161 | 351 | 45% | 1e-35 | 69% | |

TABLE 2

Comparison analysis (blastp) of the amino acid sequence of AgaB1

| Gene | Protein ID | Amino acid length | Score | Expect | Identities | Positives | Gaps |
|---|---|---|---|---|---|---|---|
| Agarase [*Pseudoalteromonas atlantica* T6c] | gb|ABG40489.1| | 793 | 959 bits (2479) | 0.0 | 451/714 (63%) | 568/714 (79%) | 6/714 (0%) |
| beta-agarase [*Alteromonas* sp. E-1] | dbj|BAE97587.1| | 798 | 932 bits (2408) | 0.0 | 445/776 (57%) | 578/776 (74%) | 16/776 (2%) |
| beta-agarase [Saccharophagus degradans 2-40] | gb|ABD81904.1| | 793 | 905 bits (2338) | 0.0 | 425/722 (58%) | 549/722 (76%) | 5/722 (0%) |
| beta-agarase [Saccharophagus degradans 2-40] | gb|ABD80438.1| | 777 | 800 bits (2065) | 0.0 | 378/713 (53%) | 512/713 (71%) | 13/713 (1%) |
| Agarase [*Pseudoalteromonas atlantica* T6c] | gb|ABG41155.1| | 782 | 753 bits (1943) | 0.0 | 363/709 (51%) | 486/709 (68%) | 13/709 (1%) |
| AguE, AguA, AguJ [uncultured bacterium] | gb|AAP49317.1| gb|AAP49347.1| gb|AAP70364.1| | 772 | 725 bits (1871) | 0.0 | 373/770 (48%) | 496/770 (64%) | 24/770 (3%) |
| Agarase [*Pseudoalteromonas atlantica* T6c] | gb|ABG41153.1| | 813 | 661 bits (1705) | 0.0 | 319/775 (41%) | 480/775 (61%) | 36/775 (4%) |

Figure 1B:
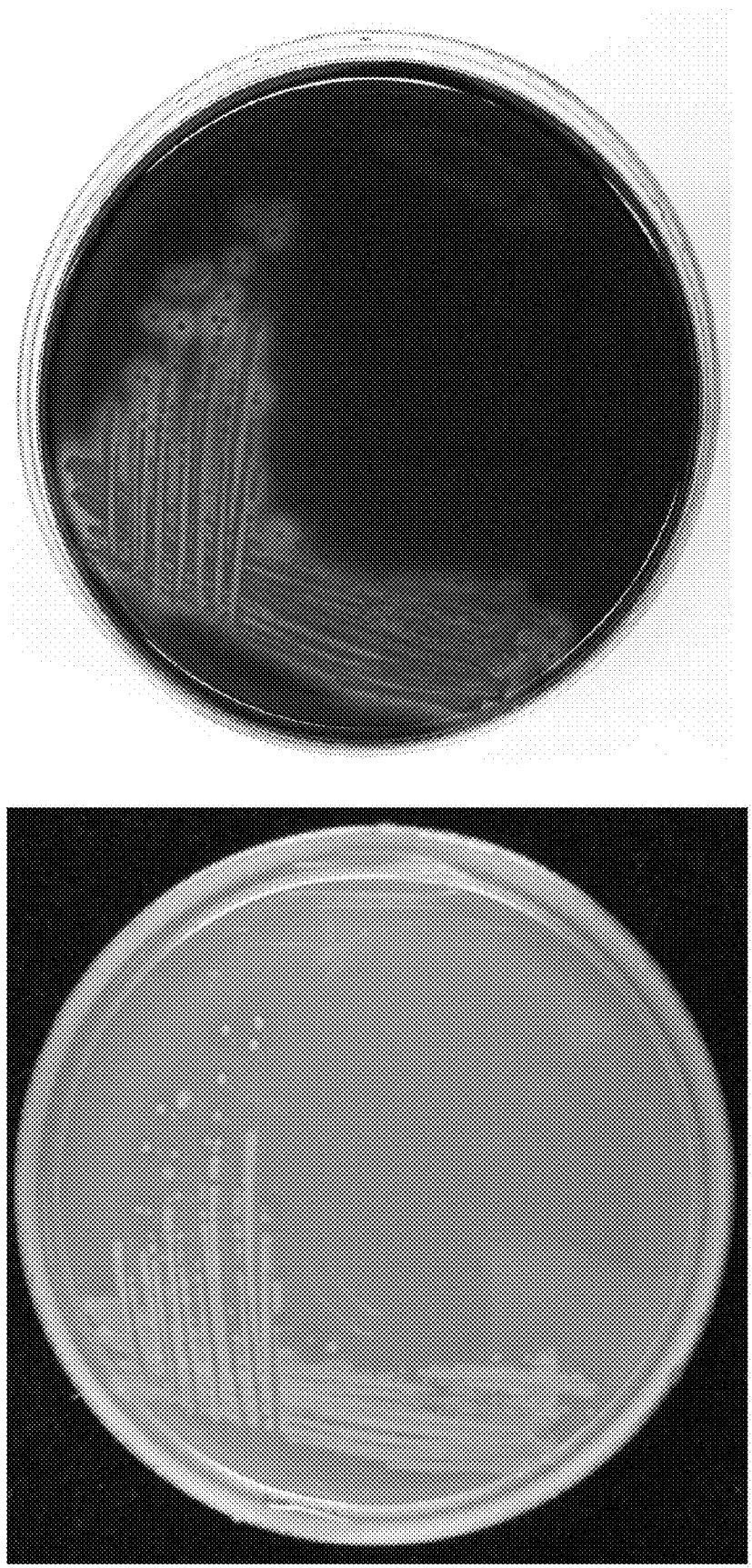
FIG. 1B shows the growth of the clone transformed by pAGAB1 on the culture plate (left) and the results of Gram's iodine reagent staining on the plate (right).
Figure 2:
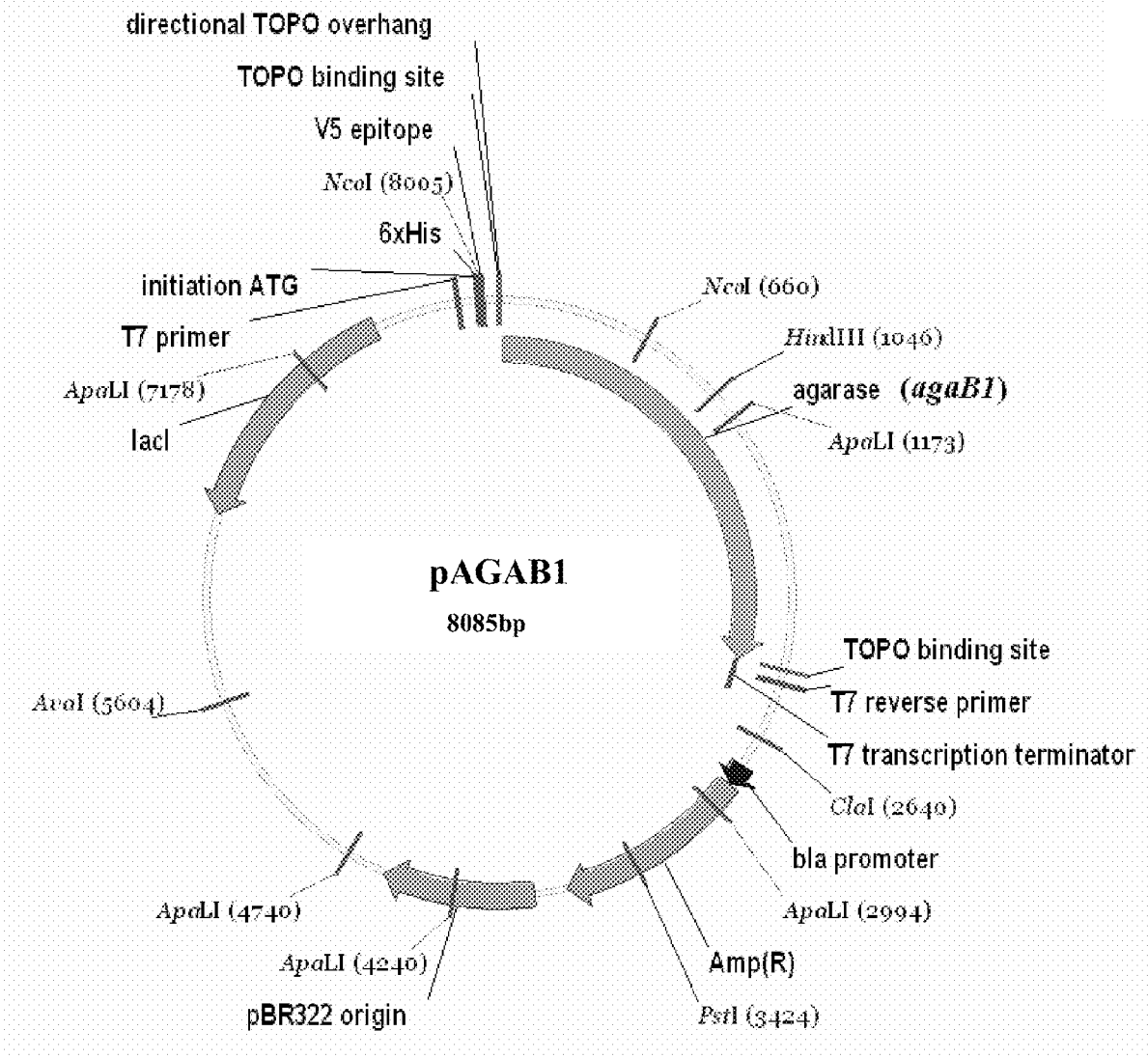
FIG. 2 shows the restriction enzyme map of pAGAB1. The agaB1 gene having a size of 2,325 bp was ligated to pET151/D-TOPO expression vector and the size of the plasmid is 8,085 bp.

The plasmid DNA was extracted by using a plasmid DNA extraction kit (Geneaid Co.), and then digested with NdeI/SacI or BglII restriction enzyme to confirm that the gene sequence inserted is agaB1. The resultant plasmid was named pAGAB1 (see FIG. 2) and transformed into *E. coli* strain BL21 (DE3). The recombinant *E. coli* was inoculated onto a LB plate (containing 0.4 mM IPTG and 100 µg/ml ampicillin) and incubated at 37° C. for 24 hours so that the decomposition of agar in the medium could be observed. The plate was stained with Gram's iodine reagent (0.05 M $I_2$ dissolved in 0.12 M KI), and the observed light yellow clear zones confirmed the agarase activity (FIG. 1B).

Example 6

Purification of Recombinant Agarase AgaB1

A single colony of pAGAB1 transformed *E. coli* strain BL21 (DE3) was picked and incubated in LB broth (containing 100 µg/ml ampicillin) at 37° C. overnight. On the next day, the culture was diluted with fresh medium until the value of $OD_{600}$ became 0.2 and the total volume became 200 ml. The diluted culture was incubated at 37° C. When the value of $OD_{600}$ reached 0.8, the culture was added with 0.1 mM IPTG and then incubated at 25° C. with shaking at 250 rpm for 6 hours to induce the expression of the recombinant agarase AgaB1 protein. The cells were collected by centrifugation at 3,500 rpm for 20 minutes.

The cells were suspended in 4 ml 5× buffer B (25 mM Tris-HCl, pH 7.4; 1 mM EDTA, pH 7.4; 250 mM sucrose) with 0.3 mg/ml lysozyme (final concentration). The mixture was placed on ice for 30 minutes. The mixture was added with 16 ml cold sterile water and then placed on ice for 20 minutes. The mixture was further added with 1 unit of Benzonase (Merck Co.) and then placed on ice for 10 minutes. A solution containing Triton X-100 and 150 mM NaCl was added to the mixture to a final concentration of 0.1%. The solution was mixed well and then centrifuged at 12,000 rpm under 4° C. for 15 minutes, and the supernatant was collected.

Ni-NTA agarose (Invitrogen Co.) was added to the supernatant and mixed on a rotor under 4° C. for 16 hours. The mixture was poured into an empty column and the unbound proteins were allowed to elute. The column was then washed with a washing buffer (30 mM imidazol; 25 mM Tris-HCl, pH 7.4; 150 mM NaCl; 1 mM PMSF), which had a volume ten-fold to that of Ni-NTA agarose, to elute the proteins with lower binding affinity. The column was further washed with an eluting buffer (250 mM imidazol; 25 mM Tris-HCl, pH 7.4; 150 mM NaCl; 1 mM PMSF) to elute agarase AgaB1. The eluted AgaB1 was collected in an Amicon ultra-15 ultracel-30K centrifuge tube (Millipore Co.) and concentrated at 2,000 rpm under 4° C. to an appropriate volume. The concentrated solution was added with 10 ml of a solution having 25 mM Tris-HCl (pH 7.4) and 150 mM NaCl, and centrifuged at 2,000 rpm under 4° C. The step was repeated four times to eliminate imidazole and to concentrate the purified recombinant AgaB1 agarase.

The concentration of the purified agarase was determined by Bradford protein assay kit (Bio-Rad). The purified agarase was diluted with double distilled water to a volume of 800 µl and then added with 200 µl Bradford reagent. The reaction solution was kept at room temperature for 15 minutes and then the value of $OD_{595}$ was measured. BSA was used as the standard to plot the standard curve. The concentration of the purified agarase was calculated with the interpolation method. It was found that 4.2 mg of AgaB1 agarase was obtained from 200 ml of cultural broth.

Example 7

Agarase Activity of AgaB1

The agarase activity was assayed by measuring the amounts of reducing sugars in the products obtained from the digestion of agar with agarase. 200 µl of 0.3% low melting agarose (dissolved in a 150 mM NaCl and 25 mM Tris-HCl buffer, pH 7.4) was incubated at 35° C. for 10 minutes. 0.4 µg of the purified AgaB1 agarase was mixed with the low melting agarose solution and incubated at 35° C. for 15 minutes. 200 µl of DNS solution (1% 3,5-dinitrosalicylic acid, 30% potassium sodium tartrate, 1.5% NaOH) was further added and then heated in boiling water for 5 minutes. After heating, the mixture was cooled in ice immediately and the value of $OD_{595nm}$ was measured by a spectrophotometer.

D-galactose (Sigma Co.) was used as the standard of reducing sugar. Various concentrations of D-galactose solutions were reacted with DNS to obtain the standard curve. On the basis of the standard curve, the $OD_{595nm}$ value of the sample treated with AgaB1 agarase was used to determine the enzyme activity. One unit (U) of agarase activity represents the production of 1 µmol reducing sugars in 1 minute under the above-mentioned conditions, i.e., 1 activity unit (U)=1 µmol D-galactose/min.

The results showed that the total enzyme activity of AgaB1 agarase obtained from 200 ml cultural broth was 136.5 U and the enzyme specific activity was 30.25 U/mg.

Example 8

Characteristics of AgaB1

(1) Molecular Weight

Figure 3:
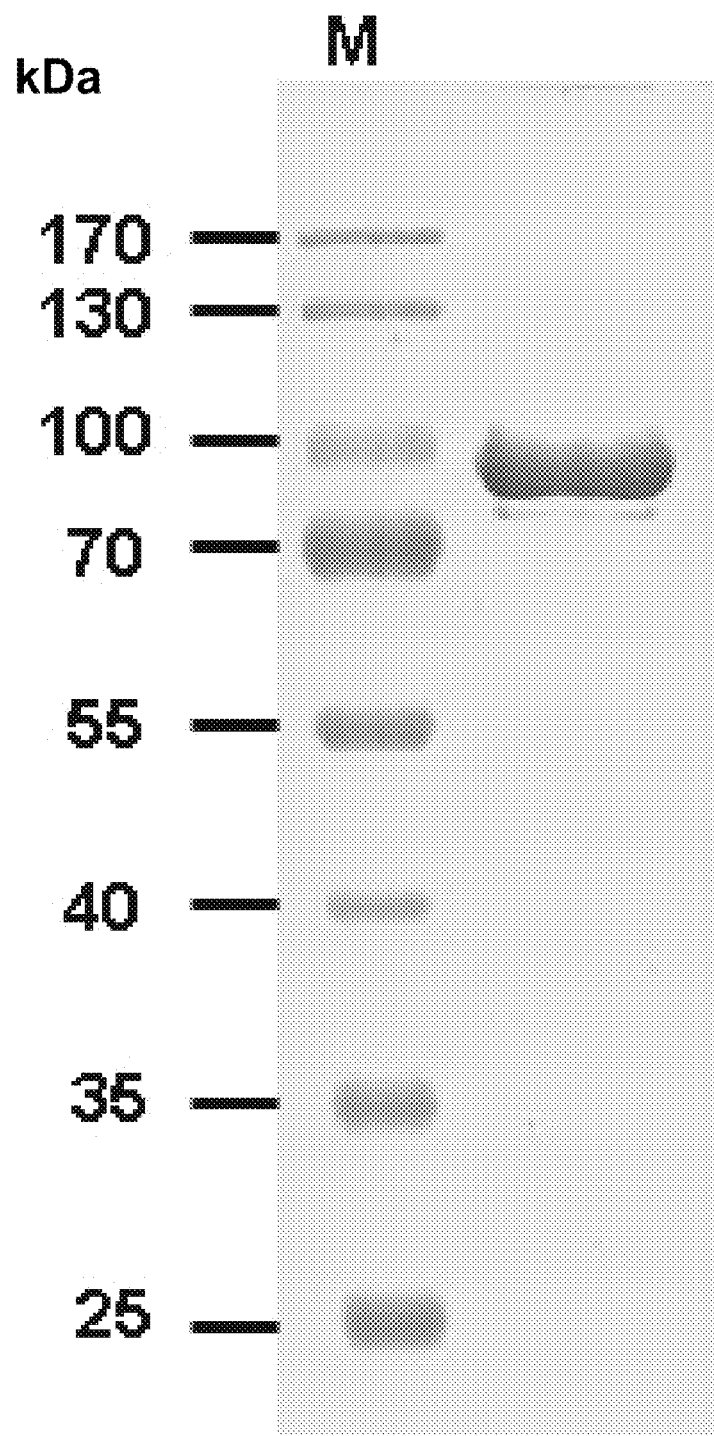
FIG. 3 shows the SDS-PAGE analysis of the purified agarase AgaB1. 3 μg of the purified recombinant AgaB1 protein was analyzed by 10% SDS-PAGE and the molecular weight of the recombinant AgaB1 protein was about 91.6 kDa. M: the PageRuler Prestain ladders SM0671 (Fermentas).

The molecular weight of the purified recombinant AgaB1 agarase analyzed by 10% SDS-PAGE electrophoresis is about 90 kDa (see FIG. 3), which is similar to the estimated molecular weight 91.6 kDa (87.6 kDa of AgaB1 protein plus 4.0 kDa of tag from pET151/D-TOPO vector).

(2) Optimum Reaction Temperature

200 µl of 0.3% low melting agarose (dissolved in 150 mM NaCl and 25 mM Tris-HCl buffer, pH 7.4) was mixed with 0.4 µg of the purified AgaB1 agarase. The AgaB1 agarase mixtures were incubated at 30, 35, 40, 45 and 50° C., respectively, for 15 minutes. The amounts of reducing sugar in each group were determined. The results are shown in the following Table 3.

TABLE 3

The relative activity of AgaB1 at different temperatures

| Reaction temperature (° C.) | Relative activity (%) |
|---|---|
| 30 | 74.4 |
| 35 | 95.7 |
| 40 | 100.0 |
| 45 | 28.2 |
| 50 | 0.0 |

It is found that the optimum reaction temperature of AgaB1 is 40° C. (defined as relative activity=100%) and the relative activity of AgaB1 at 35° C. (95.7%) is closed to that at 40° C. AgaB1 loses its activity at a temperature of 50° C.

(3) Thermal Stability

Figure 4:
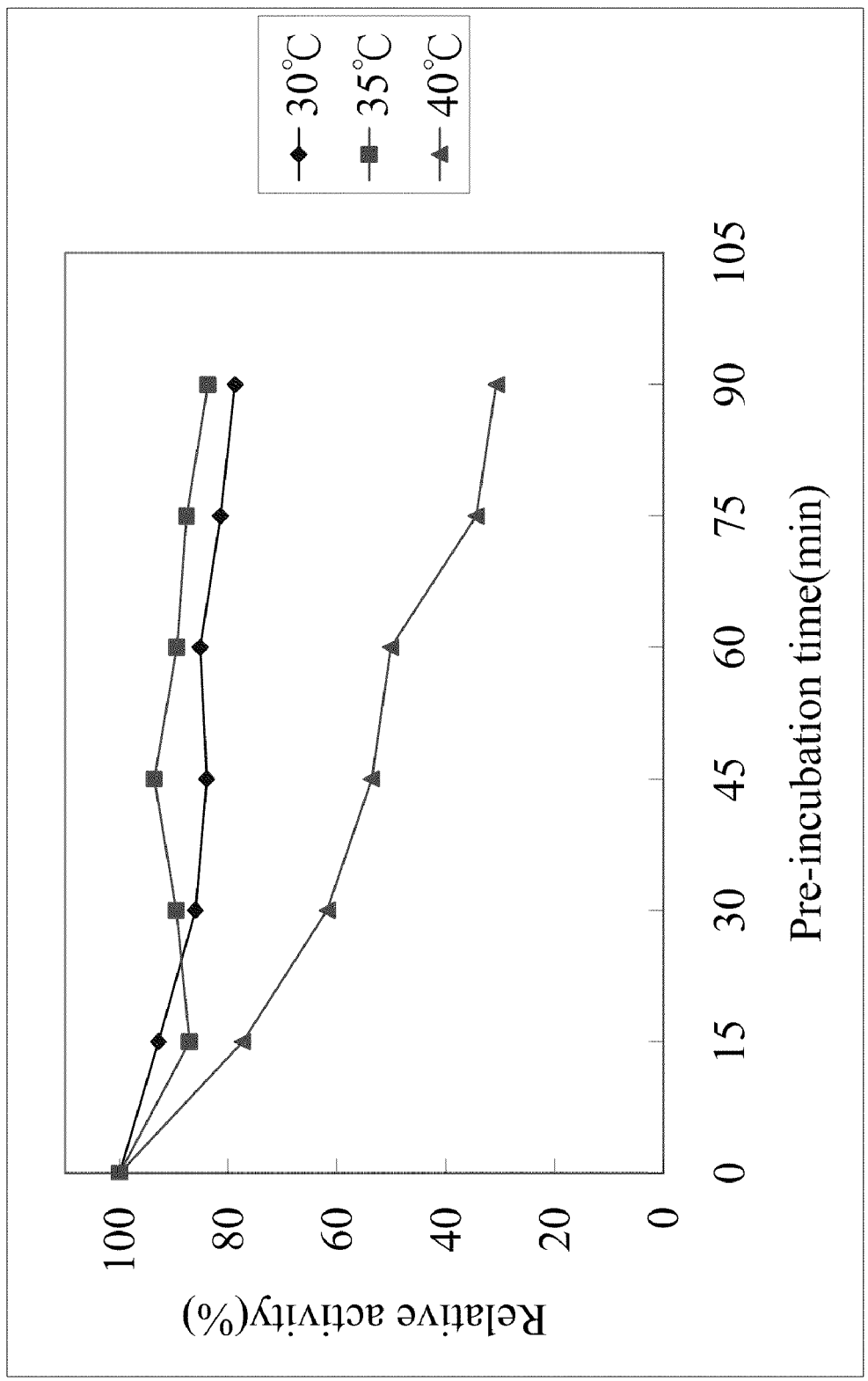
FIG. 4 shows the results of the thermal stability analysis of agarase AgaB1. The enzyme activity of the non-preincubated sample was designated as 100%.

To assay the thermal stability of AgaB1, three groups of AgaB1 agarase were incubated at 30, 35 and 40° C., respectively, for 90 minutes. During the incubation, 0.8 μg of the tested sample was taken out from each group at the following time points: 0, 15, 30, 45, 60, 75, and 90 minutes. Each sample was mixed with 200 μl of 0.3% low melting agarose (dissolved in 150 mM NaCl and 25 mM Tris-HCl buffer, pH 7.4) and incubated at 40° C. for 15 minutes. The amounts of reducing sugar in the samples taken from each group were then measured. The results are shown in FIG. 4.

In the groups of 30° C. and 35° C., the agarase activities detected at the time point 90-minute were 78.7% and 83.7%, respectively. In the group of 40° C., the agarase activities detected at the same time point decreased to 30.7%. The results indicate that although the optimum reaction temperature of agarase AgaB1 is 40° C., it is more stable at the temperature of 35° C.

Figure 5:
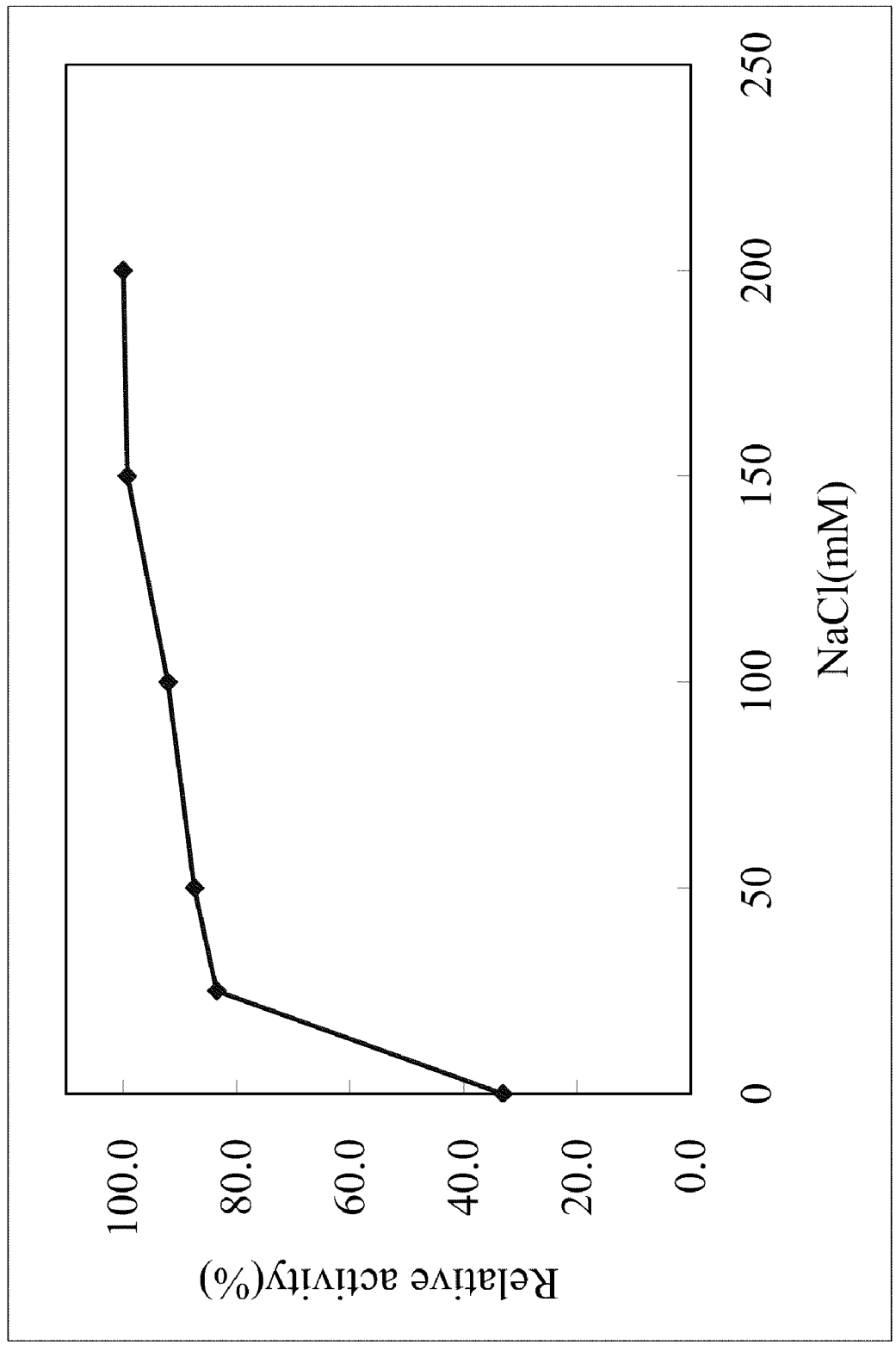
FIG. 5 shows the relative enzyme activities of agarase AgaB1 at different salt concentrations. The enzyme activity of the sample determined at 200 mM NaCl was designated as 100%.

(4) Optimum Salt Concentration 0.3% low melting agarose substrate solutions were prepared by dissolving the low melting agarose into each of the 25 mM Tris-HCl buffer (pH 7.4) solutions containing various concentrations of NaCl from 0 to 200 mM. 0.6 μg of the purified AgaB1 agarase was mixed with 200 μl each of the solutions and incubated at 35° C. for 15 minutes. The amounts of reducing sugar in each group were measured. The results are shown in FIG. 5.

In the solutions having 150 mM and 200 mM NaCl, the maximum activities of agarase are 99.2% and 100%, respectively. When the NaCl concentration is 0 mM, the relative activity is only 33.0%. When the NaCl concentration is 25 mM, the relative activity increases up to 83.4%, and it is found that the enzyme activity is in proportion to the increase in salt concentration when it is higher than 25 mM.

Figure 6:
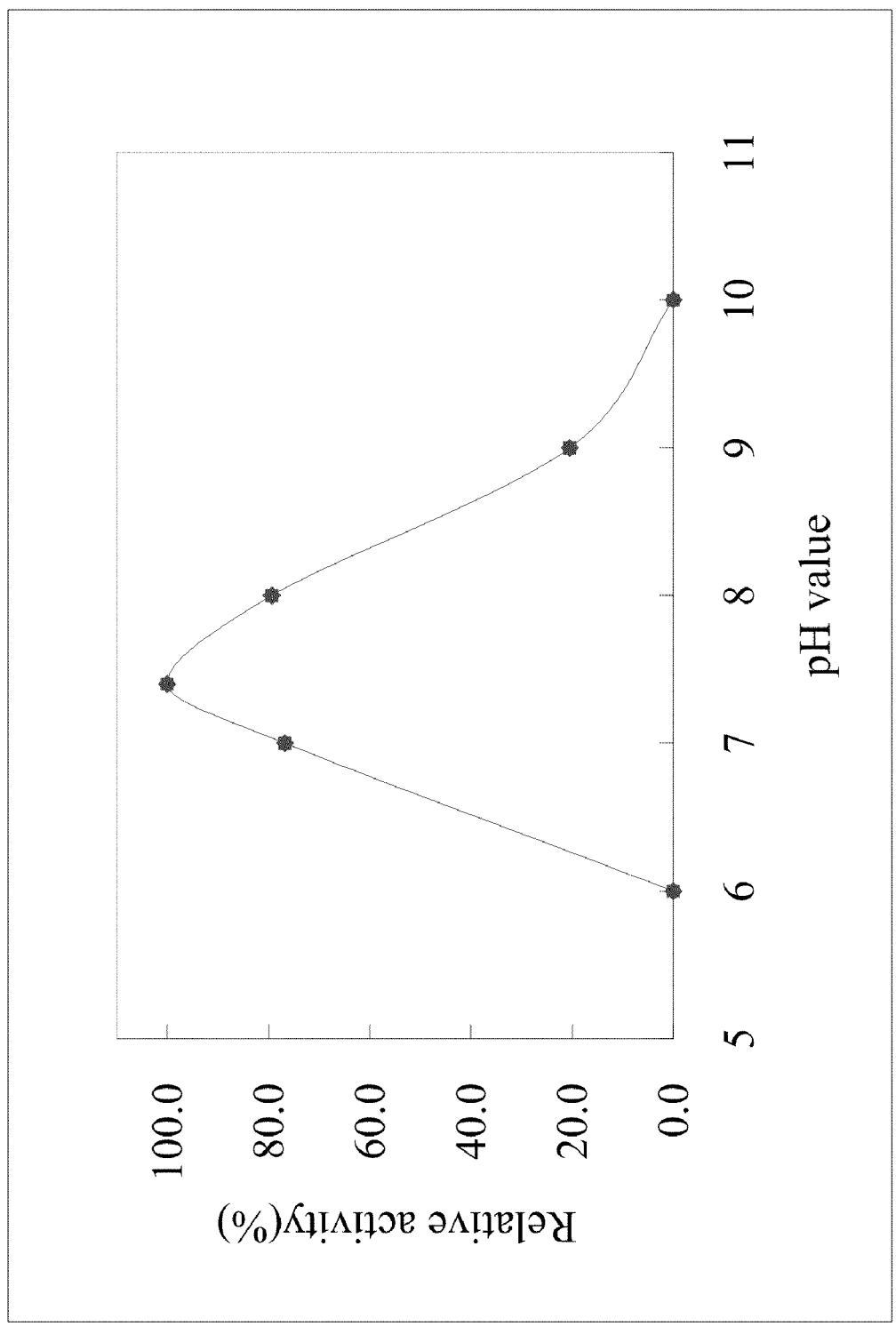
FIG. 6 shows the relative enzyme activities of agarase AgaB1 at different pH values. The enzyme activity of the sample determined at pH 7.4 was designated as 100%.

(5) Optimum Reaction pH 25 mM buffer solutions containing 150 mM NaCl with various pH values from 6.0 to 10.0 were prepared, wherein the buffer solutions of pH 6.0 and 7.0 were prepared from potassium phosphate, the buffer solutions of pH 7.4 and 8.0 were prepared from Tris-HCl, and the buffer solutions of pH 9.0 and 10.0 were prepared from glycine-NaOH. 0.3% low melting agarose substrate solutions were prepared by dissolving low melting agarose into each of the 25 mM buffer solutions. 200 μl each of the substrate solutions was heated in a drier of 40° C. for 10 minutes. Then, 0.8 μg of agarase was mixed with each of the substrate solutions and incubated at 40° C. for 15 minutes. The amounts of reducing sugar in each group were measured. The results are shown in FIG. 6.

It is found that the optimum pH of AgaB1 agarase is pH 7.4 (relative activity is 100%), and the relative activities at the pH of 7.0 and 8.0 are 91.2% and 89.7%, respectively. At pH 9.0, the relative activity is 38.7%. At the pH of 6.0 and 10.0, no detectable activity was found.

Example 9

Figure 7:
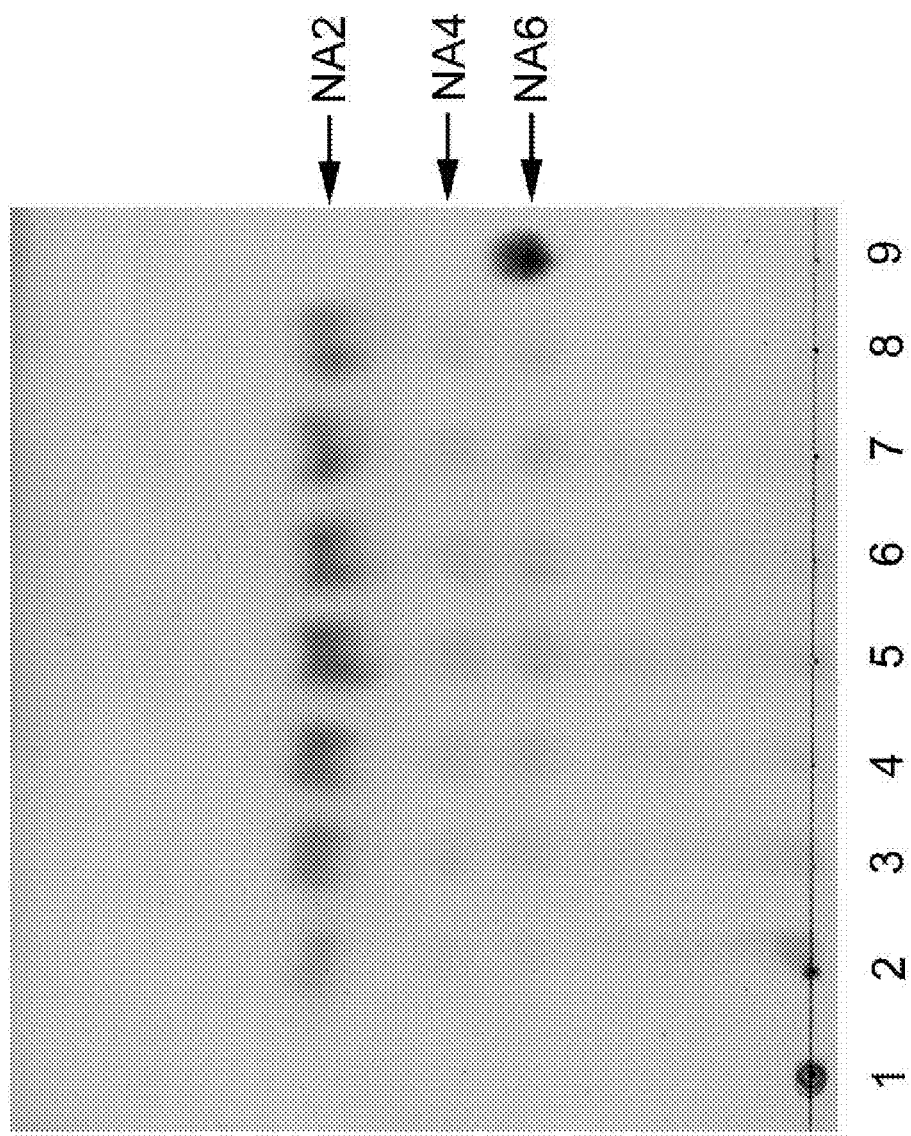
FIG. 7 shows the products from the hydrolysis of low melting agarose with agarase AgaB1 analyzed by TLC. Lanes 1 to 8 respectively represent the products at a reaction time of 0, 0.25, 0.5, 1.0, 1.5, 2.0, 3.0 and 4.0 hours. Lane 9: neoagarohexaose standard. NA2: neoagarobiose. NA4: neoagarotetraose. NA6: neoagarohexaose.

Analysis of the Hydrolysis Products (1) Thin-Layer Chromatography (TLC) Analysis 20 μg of the purified agarase was mixed with 1 ml of 1% low melting agarose (dissolved in 150 mM NaCl and 25 mM Tris-HCl buffer, pH 7.4). Nine groups of the mixture were incubated at 35° C. At 0, 0.25, 0.5, 1.0, 1.5, 2.0, 3.0, and 4.0 hours of incubation time, one group of the mixture was heated at 60° C. to inactivate the agarase. The mixture was then placed on ice for 15 minutes and centrifuged at 13,000 rpm under 4° C. for 10 minutes to remove the incompletely digested high molecular polysaccharides. The supernatant was analyzed by utilizing a Silica Gel 60 TLC plate (Merck Co.). The standard used was neoagarohexaose (Sigma Co.) and the mobile phase used was n-butanol/acetic acid/$H_2O$ (2:1:1). The TLC plate was immersed in a cerium sulfate solution (1% Cerium (IV) sulfate and 1 M $H_2SO_4$) and heated for color development. The results are shown in FIG. 7.

After incubation for 0.25 hour, hydrolysis products could be detected in the mixture. The main hydrolysis product found therein was neoagarobiose (NA2). In addition, small amounts of neoagarotetraose (NA4) and neoagarohexaose (NA6) could also be detected in the reaction mixture (see Lane 2 of FIG. 7).

Figure 8:
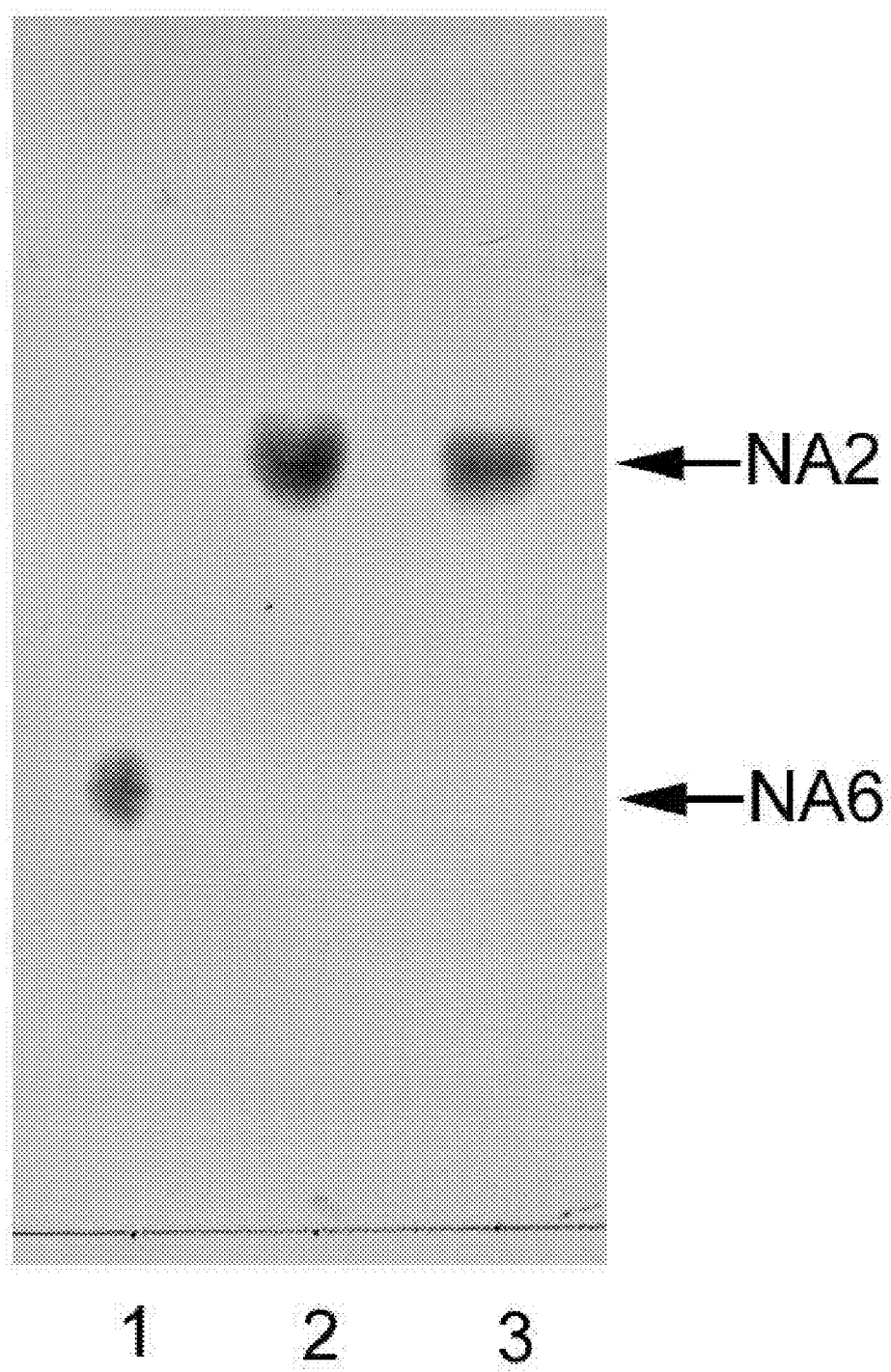
FIG. 8 shows the products of the hydrolysis of neoagarohexaose with agarase AgaB1 analyzed by TLC. Lane 1: neoagarohexaose. Lane 2: the product of 24-hour hydrolysis of neoagarohexaose with AgaB1. Lane 3: purified neoagarobiose standard. NA2: neoagarobiose. NA6: neoagarohexaose.

TLC was also used to analyze the products of the hydrolysis of neoagarohexaose with AgaB1. 10 μl of 2.5 mM neoagarohexaose (dissolved in 150 mM NaCl and 25 mM Tris-HCl buffer, pH 7.4) and 200 ng μl of the purified agarase were mixed and incubated at 35° C. for 24 hours. The reaction was then stopped by inactivating the agarase at 60° C. The products were analyzed by TLC. It is found that the main end product was neoagarobiose (see Lane 2 of FIG. 8).

(2) Mass Spectrometry Analysis

20 μg of the purified agarase was mixed with 1 ml of 1% low melting agarose (dissolved in 150 mM NaCl and 25 mM Tris-HCl buffer, pH 7.4). The mixture was incubated at 35° C. for 4 hours and then the reaction was stopped by heating at 60° C. to de-activate the agarase. The mixture was placed on ice for 15 minutes and centrifuged at 13,000 rpm under 4° C. for 10 minutes to remove the incompletely digested high molecular polysaccharides. The supernatant was analyzed by utilizing a Silica Gel 60 TLC plate, 20×10 cm (Merck Co.). The mobile phase used was n-butanol/acetic acid/$H_2O$ (2:1: 1). The portion of the TLC plate corresponding to the separated main hydrolysis product was cut off and the main product was extracted from the TLC plate by 100% methanol. The silica Gel residues in the extract were filtered out by the utilization of glass wool and 0.22 μm PVDF (Millipore). The filtered extract was concentrated by a pressure-reducing and heating method and the products contained therein were identified by using a high-performance liquid chromatograph/mass spectrometer (HPLC/MS).

The HPLC/MS system consists of a Waters model 600 pump with a controller (Miford, Mass., USA), a Waters-Micromass Quattro LC mass spectrometer (Manchester, UK), and a MassLynx 4.0 analysis software. The HPLC/MS method was performed on a Luna 3μ C18(2) column (150×2 mm id) (Phenomenex, USA). The mobile phase consisted of (A) $H_2O$+0.1% (v/v) formic acid and (B) acetonitrile+0.1% (v/v) formic acid. The Elution condition was set as follows:
Flow rate: 0.2 ml/min
Sample amount: 10 μl
Elution profile:

| Time (min) | 0~1 | 1~30 | 30~40 |
| --- | --- | --- | --- |
| Solvent A | 95% | 95~5% | 5% |
| Solvent B | 5% | 5~95% (linear gradient) | 95% |

The mass spectrometer parameters were set as follows:
Source: electrospray positive-ion (ESI+) mode
Capillary voltage: 4.5 kV
Cone voltage: 20 V Temperature:

Source: 120° C.

Desolvation: 350° C.

Nitrogen gas flow rate:

Cone: 100 l/hr

Desolvation: 500 l/hr

Collision energy for MS/MS analysis: 25V

Figure 9A:
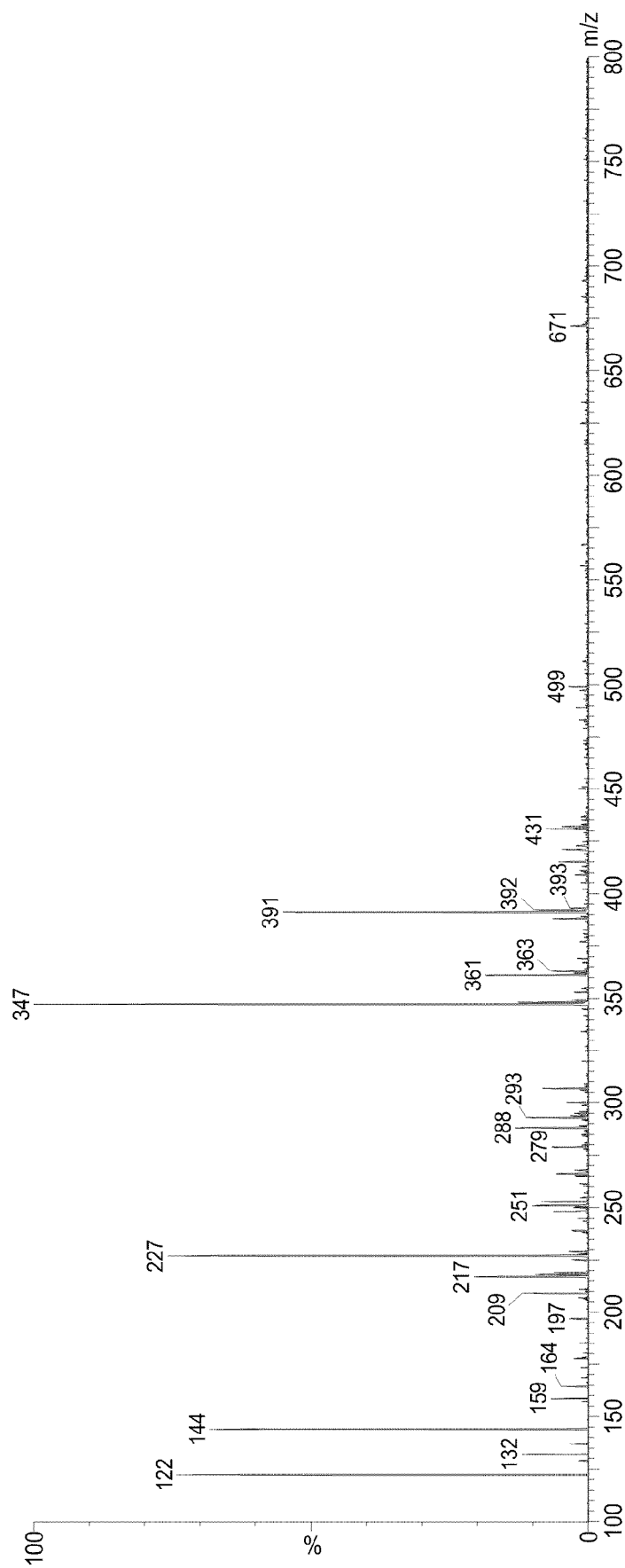
FIG. 9A shows the results of Mass scanning of the main products of the hydrolysate of low melting agarose with AgaB1.
Figure 9B:
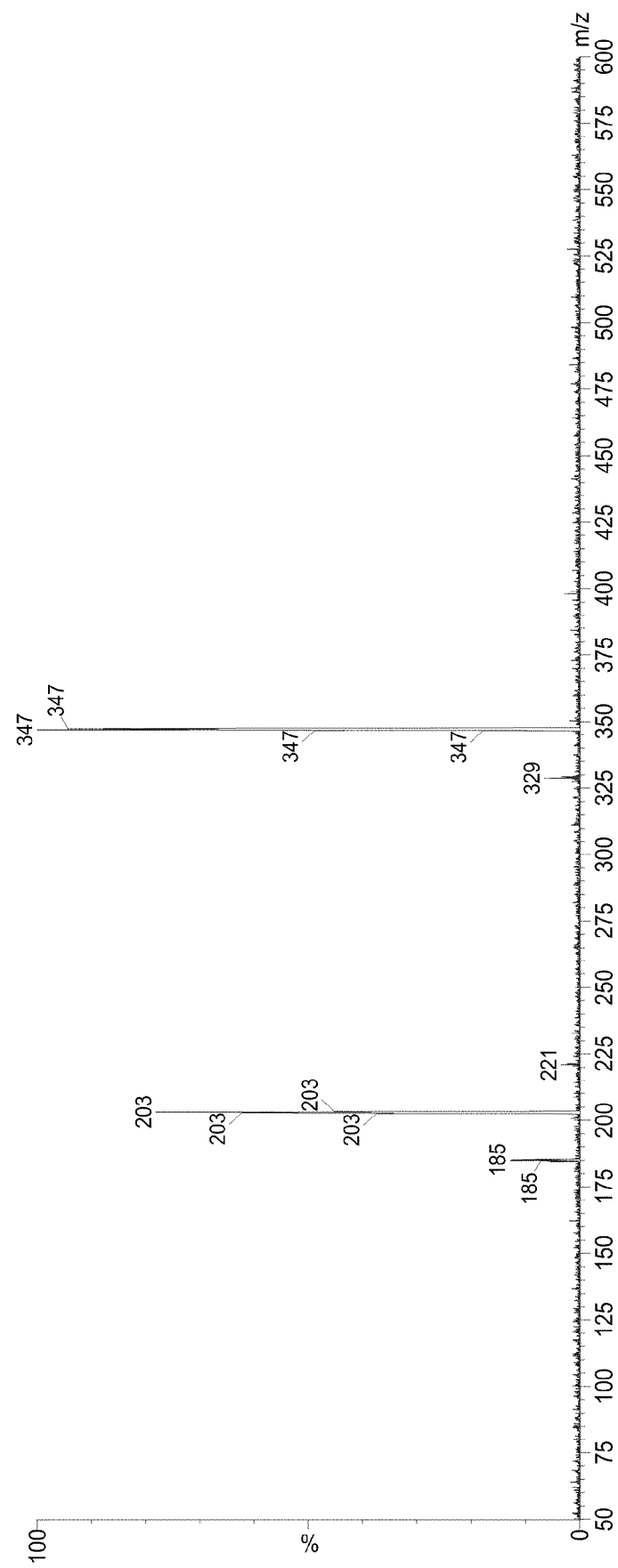
FIG. 9B shows the results of MS/MS on m/z 347 ion obtained from the Mass scanning analysis.
Figure 9C:
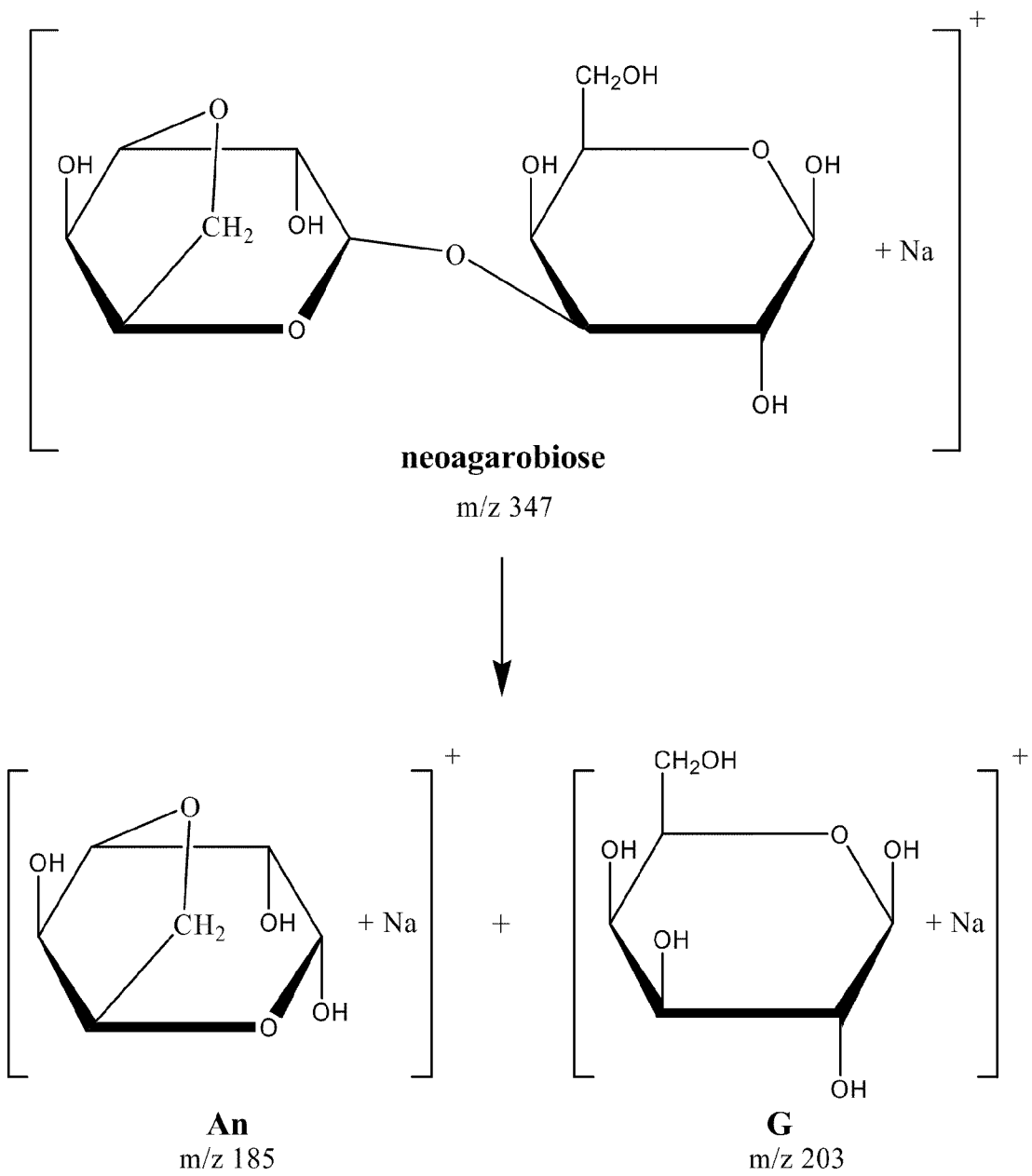
FIG. 9C shows the cleavage of [neoagarobiose+Na]$^+$ (m/z 347) on its α-1,3 linkage to form [3,6-anhydro-α-L-galactose (An)+Na]$^+$ (m/z 185) and [β-D-galactopyranose (G)+Na]$^+$ (m/z 203).

The results of the HPLC/MS scanning are shown in FIG. 9. Only one peak at the retention time of 1.91 minute was found and its mass spectrum showed a high intensity of m/z 347 ion (see FIG. 9A). The m/z 347 ion was proposed to be [neoagarobiose+Na]$^+$ because MS/MS analysis gave two major fragments, m/z 203 and m/z 185 (see FIG. 9B), wherein the m/z 203 ion should be [G-unit+Na]$^+$ fragment of neoagarobiose (G stands for galactose) and the m/z 185 ion should be [An-unit+Na]$^+$ fragment of neoagarobiose (An stands for 3,6-anhydro-α-L-galactose) (see FIG. 9C). The results of mass analyses prove that the main product of the hydrolysis of low melting agarose with AgaB1 is neoagarobiose.

Example 10

Substrate Specificity

The substrates used in the test included low melting agarose (molecular biology grade) (Sigma, cat. No. A9414), Seakem LE agarose (for electorphoresis) (Cambrex, cat. No. 50004), bacteriological agar (for preparing medium) (AGAR No. 1, Oxoid Cat No. LP0011), edible agar powder (food grade) (Chuen-Guang, Taiwan), λ-carrageenan, κ-carrageenan and ι-carrageenan (Sigma, C1138). Each substrate was dissolved in 150 mM NaCl and 25 mM Tris-HCl (pH 7.4) to prepare a solution containing 3% substrate. 200 μl each of the substrate solutions was heated in a drier of 35° C. for 10 minutes. Then, 0.6 μg of agarase AgaB1 (final concentration 3 ng/μl) was mixed with each solution and incubated at 35° C. for 15 minutes. The amounts of reducing sugar in each group were measured. The results are shown in Table 4.

It was found that the digestive activity of agarase AgaB1 to bacteriological agar was the highest one (the relative activity was designated as 100%), and the relative activities to Seakem LE agarose, edible agar powder and low melting agar were 75.9%, 70.9% and 49.3%, respectively. No digestive activity was found in λ-carrageenan, κ-carrageenan and ι-carrageenan. The results indicate that AgaB1 can hydrolyze different species of agar substrates, but not λ-carrageenan, κ-carrageenan and ι-carrageenan.

Table 4 Substrate Analysis of AgaB1

| Substrate | Relative activity (%) |
|---|---|
| Bacteriological agar (for preparing medium) | 100.0 |
| Seakem LE agarose (for electrophoresis) | 75.9 |
| Agar powder (food grade) | 70.9 |
| Low melting agarose (molecular biology grade) | 49.6 |
| λ-Carrageenan | 0.0 |
| κ-Carrageenan | 0.0 |
| ι-Carrageenan | 0.0 |

Figure 10:
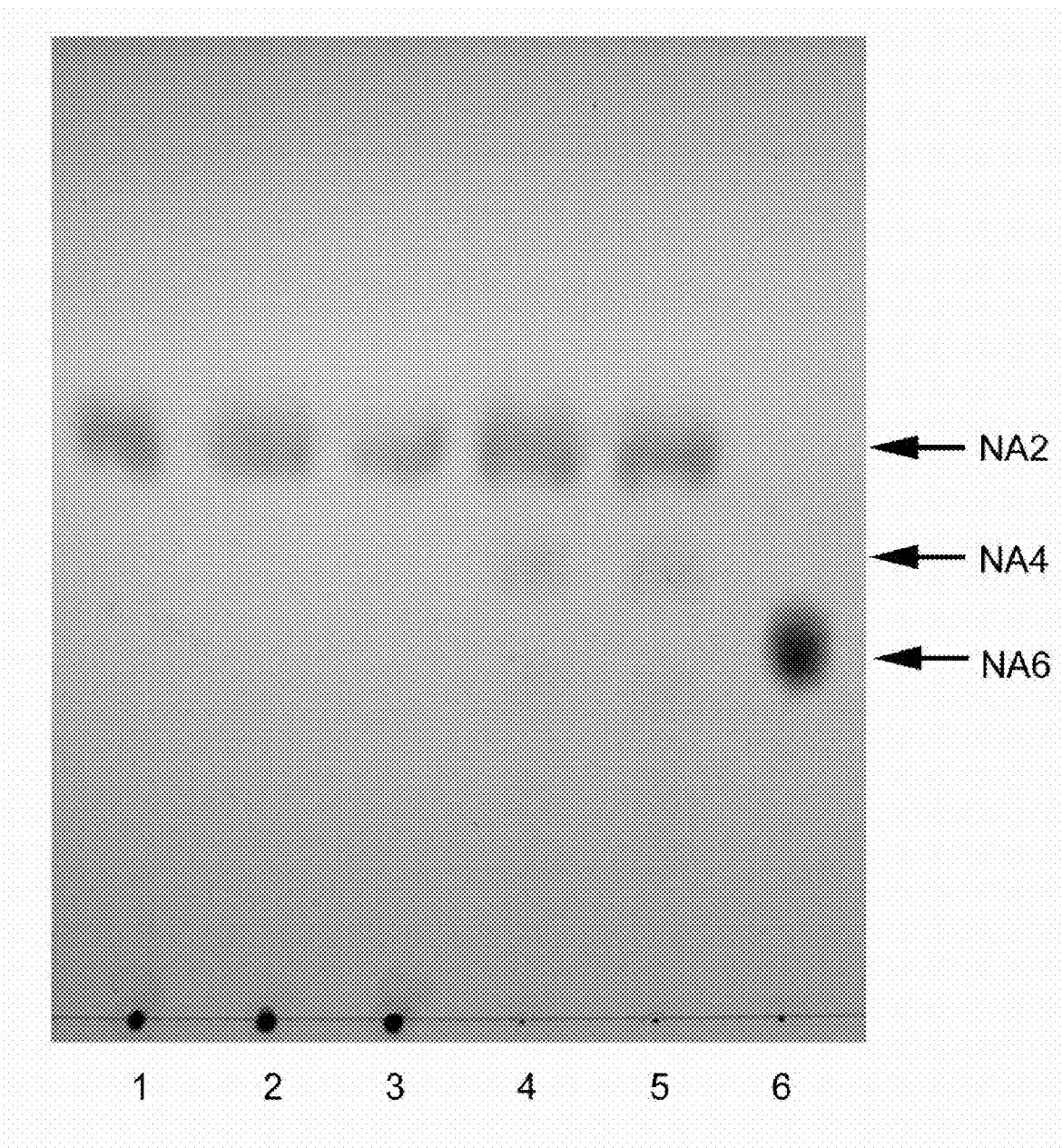
FIG. 10 shows the results of TLC analysis of the products of the hydrolysis of various agars with agarase AgaB1. Lane 1: bacteriological agar (for preparing bacterial medium). Lane 2: LE agarose (for electrophoresis). Lane 3: edible agar powder (food grade). Lane 4: low melting agarose (molecular biology grade). Lane 5: low melting agarose (Sigma). Lane 6: neoagarohexaose. NA2: neoagarobiose. NA4: neoagarotetraose. NA6: neoagarohexaose.

The products of the hydrolysis of bacteriological agar, Seakem LE agarose, edible agar powder and low melting agarose with AgaB1 were analyzed by TLC. It is found that the main product of all these substrates was neoagarobiose (see FIG. 10).

Example 10

Extraction of DNA from Agarose Gel

The DNA agarose gel samples were prepared by mixing 2.5 μg each of the DNA samples, pUC19 plasmid and Lambda DNA/HindIII maker, with 200 mg of 1% low melting agarose (dissolved in 0.5-fold TBE buffer), and placing the mixtures on ice for solidification.

The samples were heated at 70° C. for 10 minutes until the agarose melted. Then, the samples were kept in a dry bath at 35° C. for 15 minutes. 1.5 μg and 3 μg of agarase AgaB1 were mixed with each sample. The mixtures were incubated at 35° C. for 1 hour and then heated at 60° C. to inactivate the agarase. The mixtures were placed on ice for 10 minutes and centrifuged at 13,000 rpm at 4° C. for 10 minutes to remove the incompletely digested high molecular polysaccharides. In each sample, the supernatant was discarded and the precipitate was re-suspended with 0.5 ml of 70% alcohol. The suspension was centrifuged at 13,000 rpm under 4° C. for 5 minutes, and the supernatant was discarded. The precipitated DNA was vacuumed dry and then dissolved in sterile water. Equal amounts of the recovered DNA samples and 250 ng of the original DNA samples (pUC19 plasmid and Lambda DNA/Hind III maker) were applied to 1% agarose and analyzed by electrophoresis.

Figure 11A:
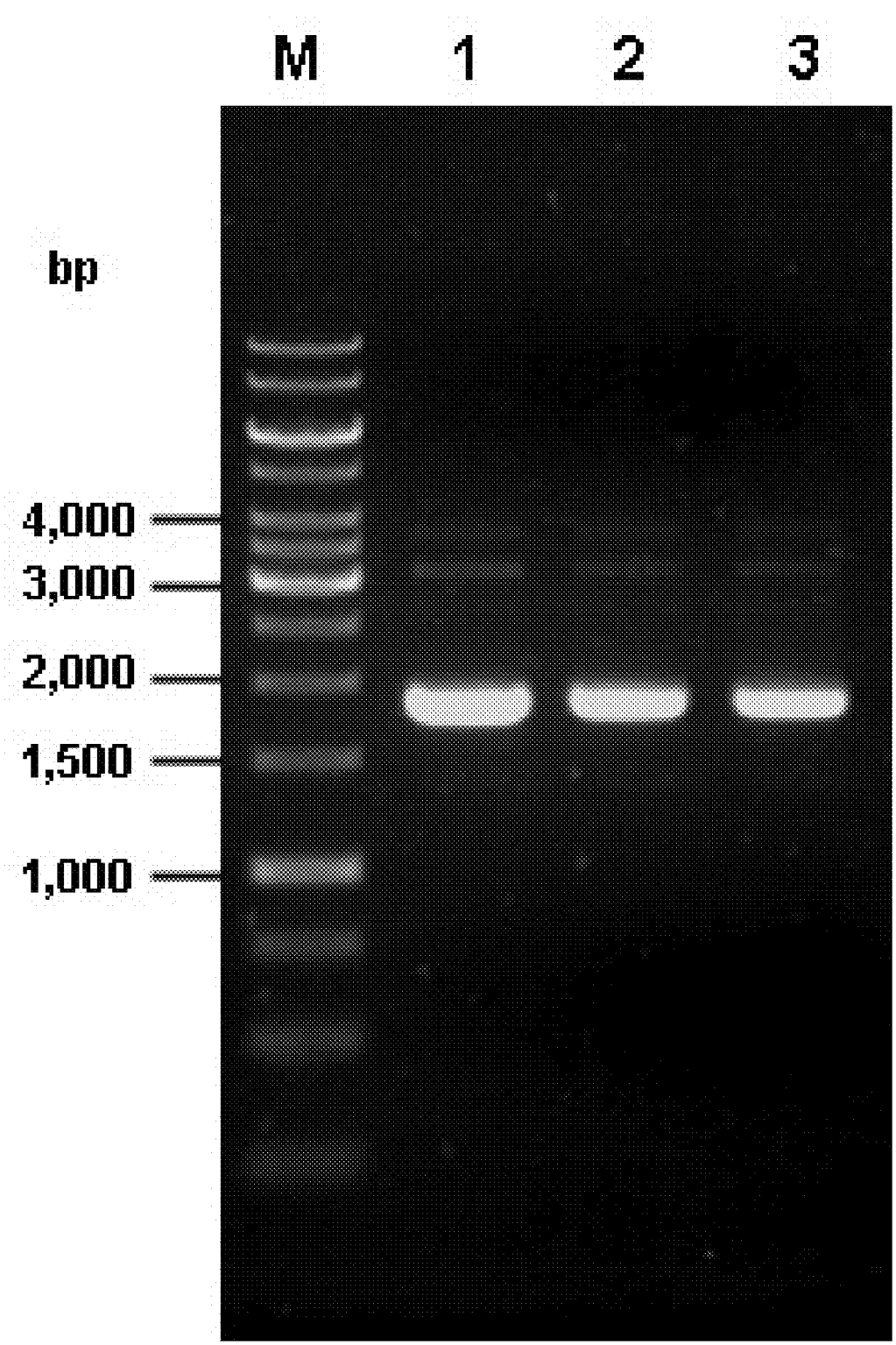
FIG. 11A shows the recovery of pUC19 plasmid DNA from low melting point agarose after agarase AgaB1 treatment. M: 1 Kb ladder (Fermentas). Lane 1: 250 ng of pUC19 plasmid. Lane 2: pUC19 sample recovered by using 1.5 μg of agarase AgaB1. Lane 3: pUC19 sample recovered by using 3 μg of agarase AgaB1.
Figure 11B:
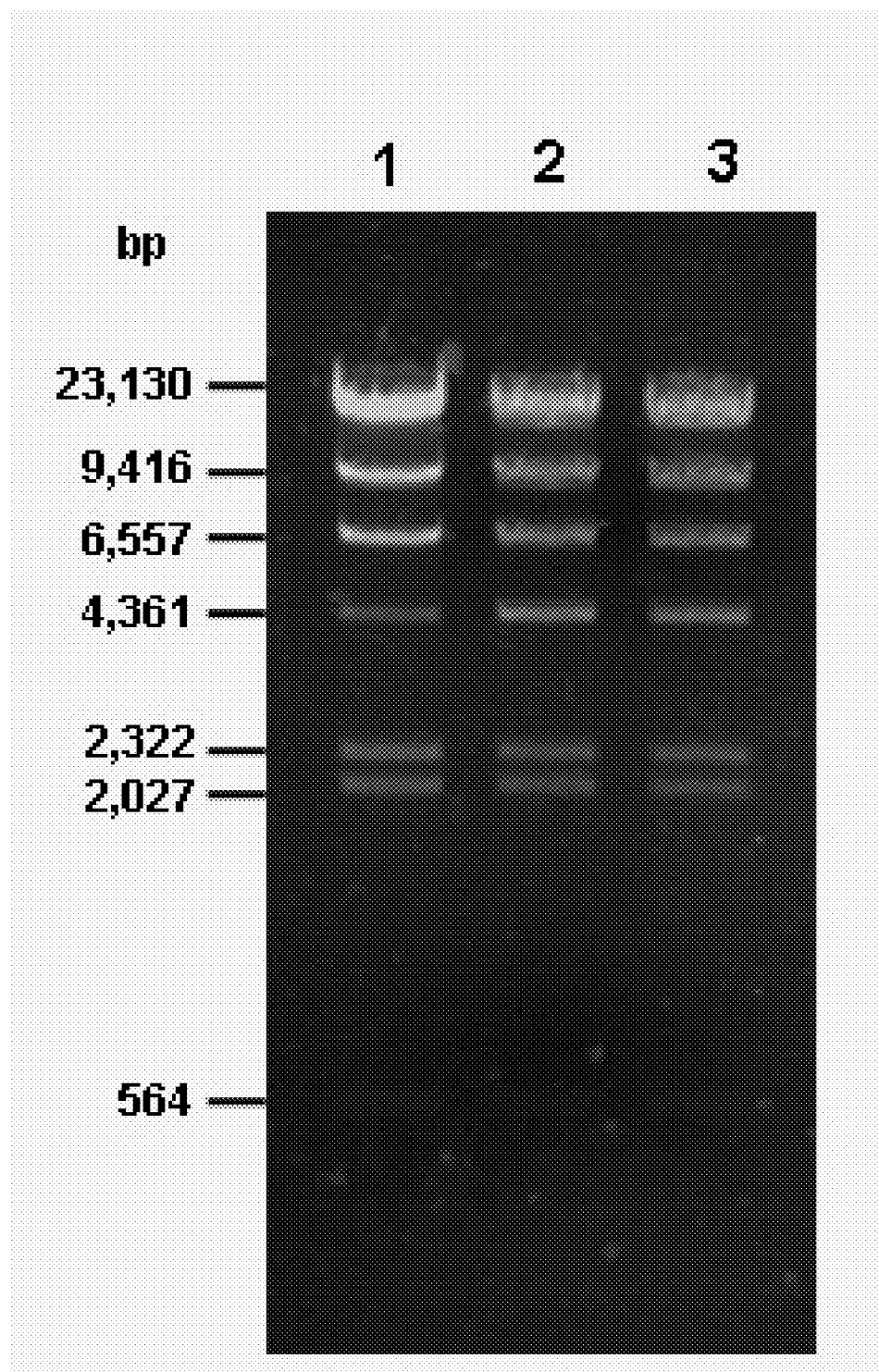
FIG. 11B shows the recovery of Lambda DNA/Hind III maker from low melting point agarose after agarase AgaB1 treatment. Lane 1: 250 ng of Lambda DNA/HindIII maker. Lane 2: Lambda DNA/HindIII maker sample recovered by using 1.5 μg of agarase AgaB1. Lane 3: Lambda DNA/HindIII maker sample recovered by using 3 μg of agarase AgaB1.

As shown in FIG. 11, all the pUC19 plasmid and Lambda DNA/Hind III maker DNA samples could be recovered from agarose gel and the recovery rate was higher than 90%. The results prove that agarase AgaB1 is suitable for recovering nucleic acid samples from agarose gel.

The invention claimed is:

1. An isolated polypeptide comprising the amino acid sequence of SEQ ID NO: 2 and having β-agarase activity.

2. The polypeptide of claim 1 further having the following physicochemical properties (a) to (e):
   (a) a molecular weight of about 87.6 kDa;
   (b) an optimum reaction temperature of about 35 to 40° C.;
   (c) an optimum reaction NaCl concentration of about 150 to 200 mM;
   (d) an optimum reaction pH of about pH 7 to 8; and
   (e) an activity of hydrolyzing agarose to neoagaro-oligosaccharides, wherein said neoagaro-oligosaccharides are predominantly neoagarobiose.

3. A method of extracting a material from agarose gel comprising:
   (a) hydrolyzing the agarose gel containing the material with the polypeptide of claim 1; and
   (b) isolating the material from the hydrolysate and purifying the same.

4. The method of claim 3, wherein the material is a nucleic acid sample.

5. The method of claim 4, wherein the nucleic acid sample is DNA or RNA.

6. A method of producing neoagaro-oligosaccharides comprising hydrolyzing agar, agarose, neoagarohexaose, neoagarotetraose, or a mixture thereof with the polypeptide of claim 1.

7. The method of claim 6, wherein the neoagaro-oligosaccarides include neoagarotetraose, neoagarohexaose and neoagarobiose.

8. The method of claim 6, wherein the neoagaro-oligosaccarides is neoagarobiose.

9. A kit for isolating and/or purifying a nucleic acid sample from agarose comprising the polypeptide of claim 1 and one or more reagents for isolating and/or purifying said nucleic acid sample.

* * * * *